US007067698B2

(12) United States Patent
Wender et al.

(10) Patent No.: US 7,067,698 B2
(45) Date of Patent: Jun. 27, 2006

(54) BI-DIRECTIONAL SYNTHESIS OF OLIGOGUANIDINE TRANSPORT AGENTS

(75) Inventors: Paul A. Wender, Menlo Park, CA (US); Christopher L. VanDeusen, Mountain View, CA (US); Kanaka Pattabiraman, Menlo Park, CA (US); Erin T. Pelkey, Phelps, NY (US); Theodore C. Jessop, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 244 days.

(21) Appl. No.: 10/211,986

(22) Filed: Aug. 2, 2002

(65) Prior Publication Data

US 2003/0073807 A1    Apr. 17, 2003

Related U.S. Application Data

(60) Provisional application No. 60/310,305, filed on Aug. 3, 2001.

(51) Int. Cl.
*C07C 277/00*     (2006.01)
(52) U.S. Cl. ............... 564/236; 514/20; 514/565; 554/53; 564/230; 564/236; 530/333; 530/345
(58) Field of Classification Search ............... 514/565, 514/20; 554/53; 564/231, 232, 236, 230; 530/345, 333
See application file for complete search history.

(56) References Cited

U.S. PATENT DOCUMENTS

| | | | | |
|---|---|---|---|---|
| 4,694,086 A | * | 9/1987 | Morimoto et al. | 564/236 |
| 5,627,194 A | * | 5/1997 | Rakhit et al. | 514/315 |
| 6,063,819 A | * | 5/2000 | Marangos et al. | 514/634 |
| 6,132,706 A | * | 10/2000 | Hider et al. | 424/78.08 |
| 6,251,433 B1 | * | 6/2001 | Zuckermann et al. | 424/486 |
| 6,380,358 B1 | | 4/2002 | Goodman et al. | 530/334 |
| 6,468,986 B1 | * | 10/2002 | Zuckermann et al. | 514/44 |
| 6,486,148 B1 | * | 11/2002 | Savage et al. | 514/182 |
| 6,495,663 B1 | * | 12/2002 | Rothbard et al. | 530/329 |
| 6,590,137 B1 | * | 7/2003 | Mitchell et al. | 604/372 |
| 6,593,292 B1 | * | 7/2003 | Rothbard et al. | 514/2 |
| 6,617,142 B1 | * | 9/2003 | Keogh et al. | 435/174 |
| 6,623,576 B1 | * | 9/2003 | Mitchell et al. | 156/62.2 |
| 6,706,765 B1 | * | 3/2004 | Tomczuk et al. | 514/605 |
| 6,759,387 B1 | * | 7/2004 | Rothbard et al. | 514/2 |
| 6,767,904 B1 | * | 7/2004 | Savage et al. | 514/182 |

FOREIGN PATENT DOCUMENTS

WO    WO 00/74701 A3    12/2000
WO    WO 01/13957 A3     3/2001

OTHER PUBLICATIONS

Mitchinson (J. Chem. Soc. Commun. 2613-2614, 1994).*
Appella et al. (1999), "Synthesis and Structural Characterization of Helix-Forming β-Peptides: trans-2-Aminocyclopentanecarboxylic Acid Oligomers." *J. Am. Chem. Soc. 121*(33);7574-7581.
Atherton et al. (1983), "Side Chain Protected $N^\alpha$-Fluorenylmethoxycarbonylamino-acids for Solid Phase Peptide Synthesis. $N^\alpha$-Fluorenylmethoxycarbonyl-$N^G$-4-methoxy-2,3,6-trimethylbenzenesulphonyl-L-arginine," *J. Chem Soc. Chem. Commun.*, pp. 1060-1062.
Atherton et al. (1989), *Solid-Phase Peptide Synthesis*; IRL Press at Oxford University Press, Oxford, England.
Bernatowicz et al. (1992), "1H-Pyrazole-1-carboxamidine Hydrochloride: An Attractive Reagent for Guanylation of Amines and Its Application to Peptide Synthesis," *J. Org. Chem. 57*(8):2497-2502.
Boger et al. (1989), "Total Synthesis of K-13," *J. Org. Chem. 54*(11):2498-2502.
Carpino et al. (1993). "The 2,2,4,6,7-Pentamethyldihydrobenzofuran-5-sulfonyl Group (Pbf) as Arginine Side Chain Protectant," *Tetrahedron Letters 34*(49):7829-7832.
Chakraborty et al. (2000), "Synthesis and Structural Studies of Oligomers of 6-amino-2,5-anhydro-6-deoxy-D-mannonic Acid," *Tetrahedron Letters 41*:8167-8171.
Feichtinger et al. (1998), "Diprotected Triflylguanidines: A New Class of Guanidinylation Reagents," *J. Org. Chem 63*(12):3804-3805.
Fields et al. (1990), "Solid Phase Peptide Synthesis Utilizing 9-fluorenylmethoxycarbonyl Amino Acids," *Int. J. Peptide Protein Res. 35*:161-214.
Hungerford et al. (2000), "Tetrahydrofuran Amino Acids: Secondary Structure in Tetrameric and Octameric Carbopeptoids Derived from a D-allo 5-(aminomethyl)-tetrahydrofuran-2-carboxylic Acid," *J. Chem. Soc., Perkin Trans. 1*, pp. 3666-3679.
Kim et al. (1985). "A Simple and Mild Esterification Method for Caboxylic Acids Using Mixed Carboxylic-Carbonic Anhydrides," *J. Org. Chem., 50*(5):560-565.
Lindgren et al. (2000). "Cell-Penetrating Peptides," *Trends Pharmacol. Sci. 21*:99-103.
Luedtke et al. (2000). "Guanidinoglycosides: A Novel Family of RNA Ligands," *J. Am. Chem. Soc. 122*(48):12035-12036.

(Continued)

*Primary Examiner*—David Lukton
(74) *Attorney, Agent, or Firm*—Carol A. Schneider; Reed IP Law Group

(57) ABSTRACT

Synthesis routes that can be adapted to large scale synthesis of oligoguanidine compounds such as oligoarginine compounds are described which use a perguanidinylation step to convert a group of ω-amino groups to the corresponding guanidinyl groups. These compounds find utility as transport agents. Modified oligoguanidine compounds are also described.

30 Claims, 3 Drawing Sheets

OTHER PUBLICATIONS

Merrifield (1963), "Solid Phase Peptide Synthesis. I. The Synthesis of a Tetrapeptide," *J. Am. Chem. Soc. 85*:2149-2154.

Mitchell et al. (2000). "Polyarginine Enters Cells More Efficiently than Other Polycationic Homopolymers," *J. Peptide Res. 56*:318-325.

Prochiantz (2000). "Messenger Proteins: Homeoproteins, TAT and Others," *Current Opinion in Cell Biology 12* 400-406.

Ramage et al. (1991). "An Acid Labile Arginine Derivative for Peptide Synthesis: $N^G$-2,2,5,7,8-Pentamethylchroman-6-sulphonyl-L-arginine," *Tetrahedron 47*(32):6353-6370.

Rothbard et al. (2000), "Conjugation of Arginine Oligomers to Cyclosporin A Facilitates Topical Delivery and Inhibition of Inflammation," *Nature Medicine 6*(11):1253-1257.

Sakarellos et al. (1978), "Synthesis of a Cyclic Charge Transfer Labeled Analogue of the Luteinizing Hormone-Releasing Factor," *J. Org. Chem. 43*(2):293-296.

Schwartz et al. (2000), "Peptide-Mediated Cellular Delivery," *Current Opinion in Molecular Therapeutics 2*(2):162-167.

Schwarze et al. (2000), "*In Vivo* Protein Transduction: Intracellular Delivery of Biologically Active Proteins, Compounds and DNA," *Trends Pharmacol Sci. 21*:45-48.

Schwarze et al. (2000), "Protein Transduction: Unrestricted Delivery into All Cells?," *Trends in Cell Biology 10*:290-295.

Wender et al. (2000), "The Design, Synthesis, and Evaluation of Molecules that Enable or Enhance Cellular Uptake: Peptoid Molecular Transporters," *Proc. Natl. Acad. Sci. USA 97*(24):13003-13008.

Zhang et al. (1992), "Nanoarchitectures. I. Controlled Synthesis of Phenylacetylene Sequences," *J. Amer. Chem. Soc. 114*(6):2273-2274.

Wender et al. (2002), "Oligocarbamate Molecular Transporters: Design, Synthesis, and Biological Evaluation of a New Class of Transporters for Drug Delivery," *J. Am. Chem. Soc. 124*(45):13382-13383.

* cited by examiner

US 7,067,698 B2

BI-DIRECTIONAL SYNTHESIS OF OLIGOGUANIDINE TRANSPORT AGENTS

CROSS REFERENCE TO RELATED APPLICATIONS

This application claims priority under 35 U.S.C. § 119(e)(1) to U.S. Provisional Application Ser. No. 60/310,305 filed Aug. 3, 2001.

ACKNOWLEDGEMENT OF GOVERNMENT SUPPORT

A portion of the work described herein was supported the National Institute of Health (CA 31841, CA 31845) and a National Institute of Health Fellowship (CA 80344). The Government may have rights in certain aspects of the invention.

FIELD OF THE INVENTION

This invention relates to the synthesis of oligoguanidine compounds. More specifically, the invention relates to the synthesis of oligoarginine compounds that find utility as transport agents.

BACKGROUND OF THE INVENTION

While considerable structural diversity is found among drugs and probe molecules, the physical properties of most of these agents with intracellular targets are restricted to a narrow range to ensure transport through the polar extracellular milieu and the non-polar lipid bilayer of the cell. Agents falling outside of this range must be tuned often through iterative analogue synthesis to achieve the optimum balance of water solubility and passive membrane transport. A promising approach directed at improving or enabling the cellular uptake of drugs, drug candidates, or probe molecules possessing a wider range of physical properties involves the use of peptide-based molecular transporters to carry these agents actively into cells. See Wender et al., *Proc. Natl. Acad. Sci. USA* 97:13003–13008 (2000); Mitchell et al., *J. Peptide Res.* 55:318–325 (2000); Prochiantz, *Curr. Opin. Cell Biol.* 12:400–406 (2000); Lindgren et al., *Trends Pharmacol. Sci.* 21:99–102 (2000); Schwartz et al., *Curr. Opin. Mol. Ther.* 2:162–167 (2000); Schwarze et al., *Trends Pharmacol Sci.*, 21, 45–48 (2000); and Schwarze et al., *Trends Cell Biol.* 10:290–295 (2000). Representative of this approach, homooligomers (7–9 mers) of L-arginine upon conjugation to various probe molecules (e.g., fluorescein) or drugs (e.g., cyclosporin A) provide highly water soluble conjugates that rapidly enter cells (e.g., human Jurkat). See Wender et al., *Proc. Natl. Acad. Sci. USA* 97:13003–13008 (2000) and Mitchell et al., *J. Peptide Res.* 55:318–325 (2000). In addition, drug conjugates of these arginine transporters have been shown to exhibit significant penetration into human skin and to release their drug cargo in targeted T cells (Rothbard et al., *Nature Medicine* 6:1253–1257 (2000)).

The enormous potential of arginine based molecular transporters is limited for several applications mainly by their availability and cost. Such homooligopeptides are usually prepared using solid-phase peptide synthesis (e.g., Merrifield, *J. Am. Chem. Soc.* 85:2149–2154 (1963); Atherton et al., *Solid-Phase Peptide Synthesis*; IRL: Oxford, Engl. (1989); and Fields et al., *Int. J. Pept. Prot. Res.* 35:161–214 (1990)). Although this approach is readily automated and allows for the synthesis and purification of long peptides, it suffers drawbacks including high cost, limited scalability, and the need for resin attachment and cleavage. In contrast, solution phase synthesis avoids the cost and scale restrictions of resins and in the particular case of oligomers can be conducted using a step-saving bidirectional strategy. Illustrative of the latter point, the uni-directional synthesis of an octamer employing solid phase synthesis requires 14 steps (one coupling and deprotection step for each added monomer), whereas a solution phase bi-directional synthesis of the same octamer would require only seven steps (three coupling and four deprotection steps). See, for example, Appella et al., *J. Am. Chem. Soc.* 121:7574–7581 (1999); Hungerford et al., *J. Chem. Soc., Perkin Trans. I*, 3666–3679 (2000); and Chakraborty et al., *Tetrahedron Lett.* 41:8167–8171 (2000). In the specific case of arginine based peptides, solution phase synthesis offers the additional advantage of avoiding the use of expensive protecting groups for the guanidinium subunit (e.g., Mtr, Pmc and Pbf; see, respectively, Atherton et al., *J. Chem Soc. Chem. Commun.*, 1062–1063 (1983); Ramage et al., *Tetrahedron* 47:6353–6370 (1991); and Carpino et al., *Tetrahedron Lett.* 34:7829–7832 (1993)) required in solid phase synthesis.

However, in spite of the advances in the art, there remains a need for a method for the preparation of arginine oligomers, or more generally oligoguanidines that is both cost effective and scalable. The present invention addresses that need.

SUMMARY OF THE INVENTION

One aspect of the invention relates to a method for the preparation of an oligoguanidine compound, comprising the steps of: (a) contacting an oligomer having a plurality of chemically tethered amines, wherein a portion of the tethered amines have attached protecting groups, with a protecting group removal agent to remove each of the protecting groups to produce an oligomer having a plurality of chemically tethered amines; and (b) contacting said oligomer having a plurality of chemically tethered amines with a guanidinylation reagent to convert each of said chemically tethered amines to a guanidinyl group to produce an oligoguanidine compound.

Another aspect of the invention provides for the further step of converting the oligoguanidine compound of step (b) to a salt, for example, a poly trifluoroacetate salt.

Yet another aspect of the invention pertains to a method for the preparation of an oligoarginine compound from a suitably protected ornithine monomer, comprising the steps of: (a) coupling two different suitably protected ornithine monomers to produce an orthogonally protected coupled ornithine compound; (b) dividing the orthogonally protected coupled ornithine compound into two portions and activating each of the portions for amide coupling to produce two independently activated coupled ornithine compounds; (c) recombining the two independently activated coupled ornithine compounds under conditions sufficient for amide coupling to produce a new orthogonally protected coupled ornithine compound; (d) subjecting the product of step c) to dividing, activating, and recombining for from zero to three times to produce an oligoornithine compound having 4, 8 or 16 ornithine monomers in a linear configuration; and (e) contacting the oligoornithine compound with a perguanidinylation reagent under conditions sufficient to produce an oligoarginine compound.

Still another aspect of the invention relates to oligoguanidine compounds produced by the aforementioned methods.

DETAILED DESCRIPTION OF THE INVENTION

I. Definitions and Nomenclature

Figure 1:
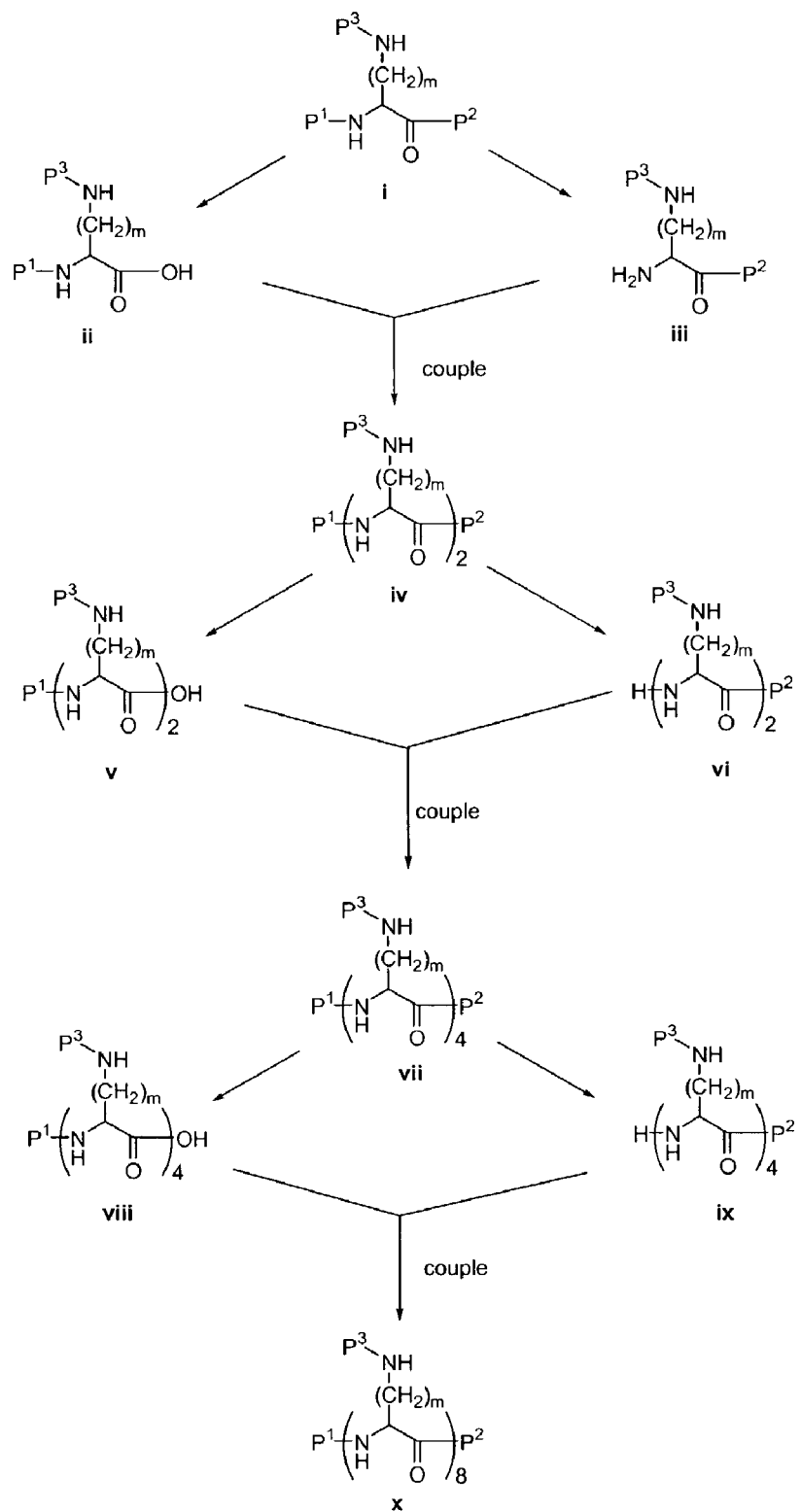
FIG. 1 illustrates a bi-directional synthesis scheme of a protected arginine octamer from a protected ornithine monomer.

Before describing detailed embodiments of the invention, it will be useful to set forth abbreviations and definitions that are used in describing the invention. The definitions set forth apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

It must be noted that, as used in this specification and the appended claims, the singular forms "a", "an" and "the" include plural referents unless the context clearly dictates otherwise. Thus, for example, reference to "a pharmacologically active agent" includes a mixture of two or more such agents, reference to "a hydroxide-releasing agent" includes mixtures of two or more such agents, and the like.

In describing and claiming the present invention, the following terminology will be used in accordance with the definitions set out below.

As used herein, the term "oligoguanidine compound" refers to an oligomer of subunits, each of which contain a chemically tethered guanidine group. Exemplary subunits include arginine and arginine-like residues, as well as repeating groups such as Gly-Arg-Gly (more generally $X^o$-Arg-$^o$ wherein each $X^o$ is an amino acid that is devoid of a guanidino group and Arg is meant to include D- or L-arginine as well as arginine-like residues). An arginine-like residue has the general structural characteristics of an arginine amino acid (including both D- and L- forms), but has up to 6 additional methylene groups between the guanidino moiety and the α-carbon of arginine, or has up to 2 fewer methylene groups between the guanidino moiety and the α-carbon of arginine. Accordingly, in one embodiment of the invention, an oligoguanidine compound has a peptide backbone and the following formula A:

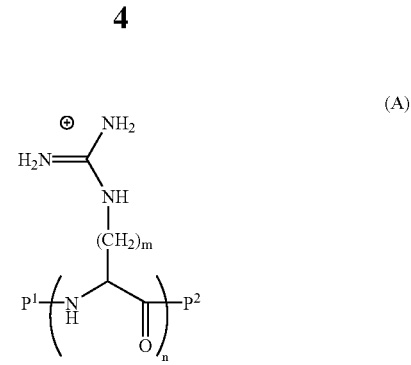

(A)

wherein: m is an integer of from 1 to 12; n is an integer of from 4 to 16; $P^1$ is H or a nitrogen protecting group; and $P^2$ is a protected or unprotected hydroxy or amino group. In the formula above, the guandino group is illustrated as being charged. One of skill in the art will appreciate that the extent to which an oligoarginine compound is charged will depend on the environment in which it is present (including medium, pH, etc.) and all charged and uncharged forms are contemplated by the present invention.

The term "oligoguanidine compound" is also intended to include numerous variations of formula A, where the tether (side chain) is modified but the terminal guanidine group (—HN—C(NH$_2$)NH unprotonated or —HN—C(NH$_2$)NH$_2^+$ protonated) remains unchanged (n, $P^1$ and $P^2$ are as defined above). Modifications to the side chain include the following substitutions:

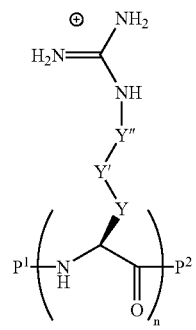

where Y, Y' and Y" are independently C, O, N, S or B derivatives. Modifications can include the positioning of double or triple bonds:

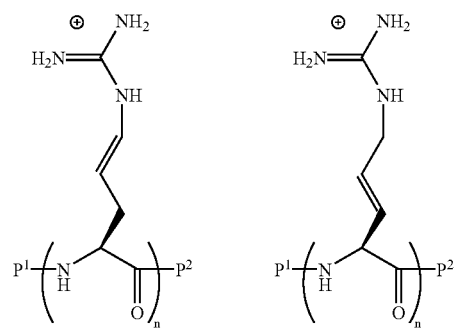

-continued

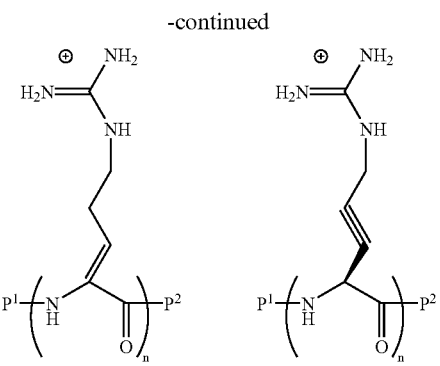

Modifications can also include the addition of cyclic structures (a=0–5), and the ring carbons may be further substituted:

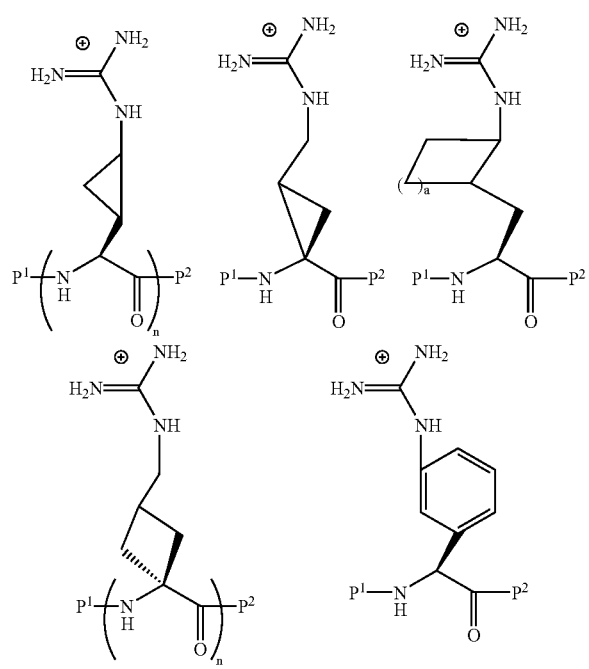

As is shown above, 2 or 3 of the carbons in the arginine side chain may be included in the cyclic structure.

The term "oligoguanidine compound" is also intended to include non-peptide variations of formula A. Examples are shown below, where G is the guanidinyl side chain, and n, $P^1$ and $P^2$ are as defined above.

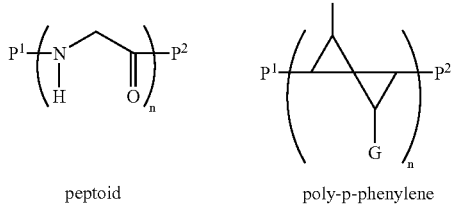

peptoid          poly-p-phenylene

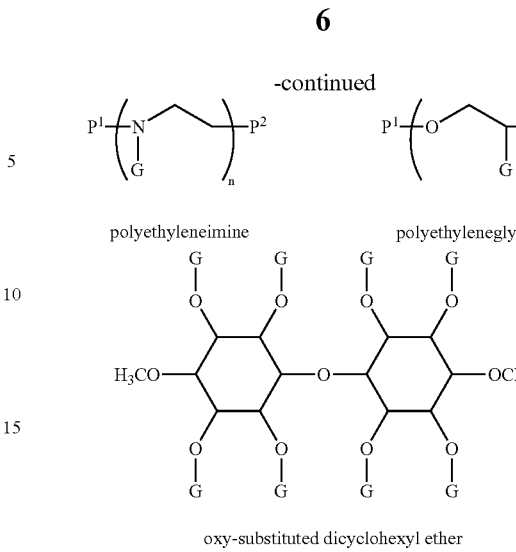

polyethyleneimine          polyethyleneglycol oxy-substituted dicyclohexyl ether The backbone may also be a peptide-peptoid hybrid, a polyamide, an azapeptide (e.g., replacing the α-carbon with nitrogen), a peptide-urea hybrid, a polyenamine ($P^1$—{N(G)—[CH2]$_v$}$_n$—$P^2$, where v is from 1–8, for example v=2 is polyethylenimine, as shown above), a polyoxamide, a hydrocarbon, a polyethylene/polypropylene ether, a carbohydrate and an oxy-substituted dicyclohexyl ether (as shown above) backbone. These non-peptide backbones may provide enhanced biological stability (for example, resistance to enzymatic degradation in vivo). The backbone can also be a cyclic peptide or non-peptide system, for example:

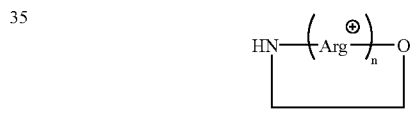

Similarly, a "polyamide oligomer having chemically tethered amines" refers to a polypeptide compound having repeating units of one, two or three amino acid residues wherein each of the repeating units has a sidechain amino group. The amino acids can be α-, β-, γ- or δ-amino acids, but are selected so that at least one of the amino acids in each subunit has a sidechain amino group (e.g., lysine, ornithine, homoornithine, and the like). In one sense the polyamide oligomer having chemically tethered amines can be a compound having the formula A':

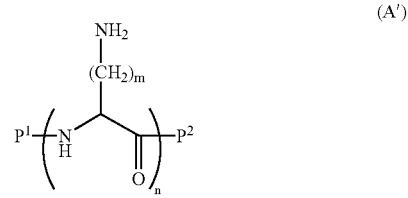

(A')

where m, n, $P^1$ and $P^2$ are as defined above, but the polyamide oligomer can also have additional amino acids that are present to provide spacing between the tethered amine residues. The side chain of the compound of formula A' can also be similarly modified as described above for formula A, while the terminal amine group remains unchanged. Additionally, oligomers of all D-isomers, all L-isomers and mixtures of D- and L-isomers are within the scope of the formulas above.

As used herein, the term "modified oligoguanidine compound" refers to an oligomer of subunits, each of which contain a chemically tethered guanidine group that has been chemically modified. Modification to the guanidine group can be done prior to the synthesis by using an appropriate starting material (i.e., an oligomer having chemically tethered "modified" amines) or while the compound is being synthesized. Alternately, an oligoguanidine compound can be made as described herein, followed by modification of the guanidine groups. Preferably, the modification occurs at the end of the synthesis. In this manner, numerous variations can be produced from a common intermediate. R can be any suitable substituent, for example, H, alkyl, hydroxyl, cyano, alkoxy, =O, =S, —NO$_2$, halo, heteroalkyl, amine, thioether, —SH, aryl and heteroalkyl.

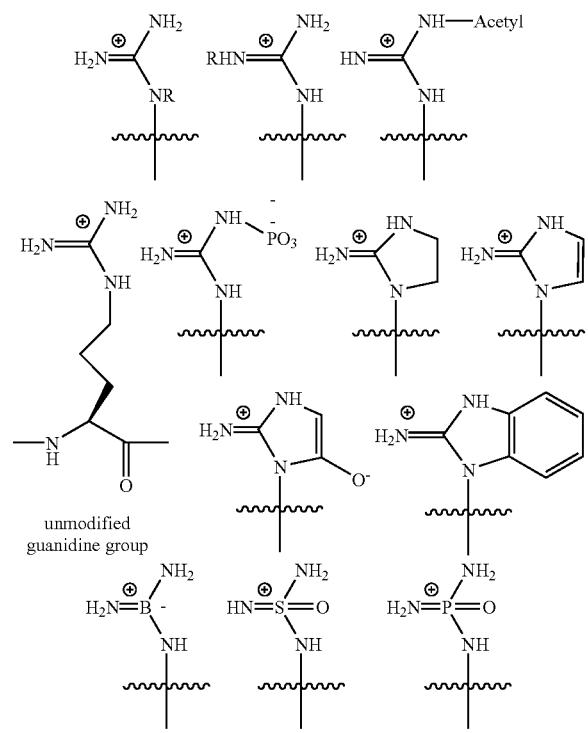

II. Abbreviations

In describing and claiming the present invention, the following abbreviations will be used in accordance with the definitions set out below.

| | |
|---|---|
| AcOH | acetic acid |
| Bn | benzyl |
| Boc | tert-butoxycarbonyl |
| DMAP | 4-(dimethylamino)pyridine |
| DMF | N,N-dimethylformamide |
| DMSO | dimethylsulfoxide |
| Et$_3$N | triethylamine |
| EtOAc | ethyl acetate |
| Fmoc | 9-fluorenylmethoxycarbonyl |
| MeOH | methanol |
| Mtr | 4-methoxy-2,3,6-trimethylbenzenesulfonyl |
| NMM | N-methylmorpholine |

-continued

| | |
|---|---|
| Orn | ornithine |
| Pbf | 2,2,4,6,7-pentamethyldihydrobenzofuran-5-sulfonyl |
| PG | protecting group |
| Pmc | 2,2,5,7,8-pentamethylchroman-6-sulfonyl |
| RP-HPLC | reverse phase high performance liquid chromatography |
| RT | room temperature |
| TFA | trifluoroacetic acid |
| THF | tetrahydrofuran |
| Z | benzyloxycarbonyl |

III. Reactions

A. General

FIG. 1 provides an illustration for the bi-directional synthesis of an arginine octamer (when m=3) beginning with an orthogonally protected ornithine compound. The protected ornithine compound i, is divided into two portions. The first portion is deprotected to provide ii, while the second portion is deprotected to provide iii. The two portions are then recombined with a suitable coupling reagent to provide the dipeptide iv. Once again, the product is divided into two portions and the first portion is deprotected on one terminus to provide v, while the second portion is deprotected on the carboxy terminus to provide vi. Compounds v and vi are then coupled to provide the protected tetrapeptide vii. One more sequence of divide into portions, selectively deprotect and couple, provides the protected octapeptide x as an intermediate for the removal of P$^3$ protecting groups and perguanidinylation chemistry provided in more detail below.

Figure 2:
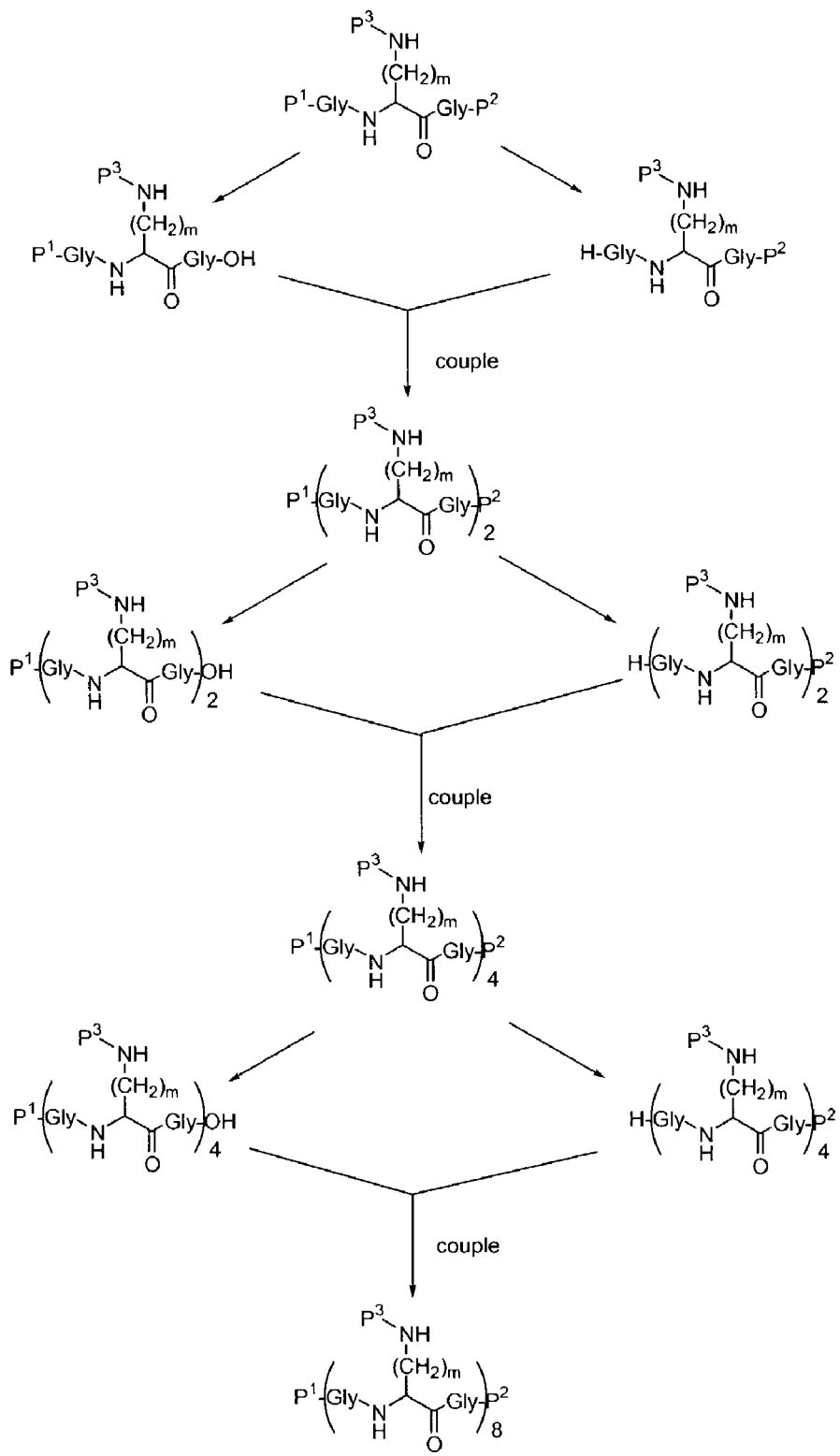
FIG. 2 illustrates a bi-directional synthesis scheme of a spaced protected arginine octamer from a protected -Gly-Orn-Gly- subunit.

FIG. 2 illustrates a similar sequence applied to a -Gly-Orn-Gly- subunit, resulting in a fully-protected form of (Gly-Orn-Gly)$_8$ (SEQ ID NO:1).

As can be seen from FIGS. 1 and 2, the bi-directional methods of the invention provide for oligomers having 2, 4, 8, 16 or 32 subunits (if carried through sufficient iterations). For longer or shorter oligomers than those just noted, any of the intermediate compounds can be deprotected and coupled to single amino acids, tripeptides, pentapeptides and the like.

Figure 3A:
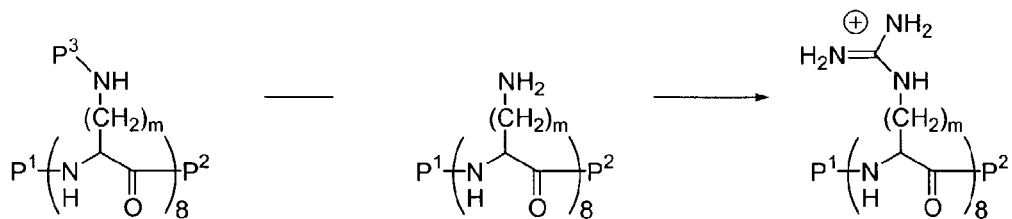
FIGS. 3A, 3B, 3C and 3D illustrate the applicability of the deprotection/perguanidinylation chemistry that is used in the present invention.

The bi-directional methods described herein produce oligoguanidine compounds by a deprotection/perguanidinylation procedure that has now been demonstrated for polyamide oligomers having a plurality of chemically tethered amines (e.g., oligomers containing lysine, ornithine, homoornithine as well as their β-, γ- and δ-amino acid counterparts). The scope of this transformation is illustrated in FIG. 3. In FIG. 3A, a suitably protected ornithine octamer is deprotected to provide the octamer having tethered amine groups as shown.

Figure 3B:

Perguanidinylation provides an arginine octamer. In one embodiment of the invention, the deprotection and perguanidinylation is carried out in a single reaction vessel as shown in FIG. 3B.

Figure 3C:
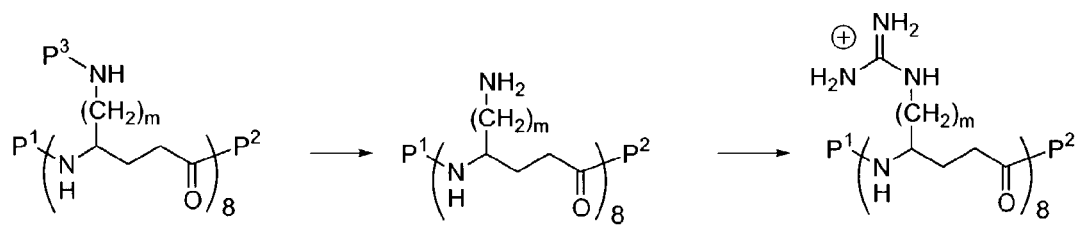
Figure 3D:
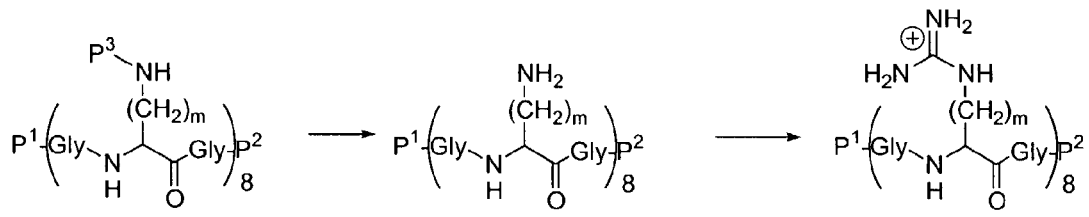

FIG. 3C illustrates the applicability to an oligomer of γ-amino acids, while FIG. 3D illustrates the applicability to spaced oligomers wherein the spacing is provided by glycine residues.

Another embodiment of the invention is illustrated in the scheme below, which shows a general formula for oligoguanidine compounds, and its application to both spaced oligoarginine compounds (derived from spaced oligomers having chemically tethered amines) and contiguous oligoarginine compounds (derived from oligoornithine compounds).

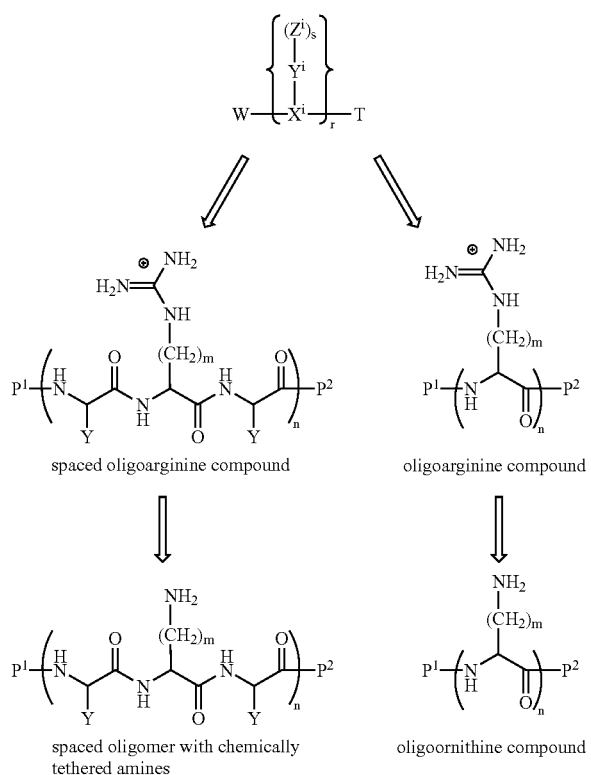

lation reagent to convert each of the chemically tethered amines to a guanidinyl group to produce an oligoguanidine compound.

In some embodiments, the polyamide oligomer having chemically tethered amines will be isolated and purified using methods such as ion exchange chromatography, HPLC, column chromatography and the like. This polyamide oligomer (tethered amine) compound can be isolated as a salt or in neutral form. However, in a preferred embodiment, the polyamide oligomer compound having chemically tethered amines is not isolated, but is carried on directly to step (b).

The method may optionally further comprise the step of converting the oligoguanidine product to a salt, for example, a poly trifluoroacetate salt.

In certain embodiments, steps (a) and (b) are carried out in the same reaction vessel, and may be carried out sequentially or concurrently. For example, an oligoornithine compound having protecting groups on each of the ω-amines can be treated with a combination of a protecting group removal agent and a guanidinylation reagent to provide the oligoarginine compound in a single step. As a result, it is not necessary for all protecting groups to be removed prior to guanidinylation of a particular amine group. In one particularly preferred embodiment, an oligoornithine compound having trifluoroacetyl protecting groups on each of the ω-amines is contacted with both a protecting group removal agent, preferably sodium carbonate, and with a guanidinylation reagent, preferably pyrazole-1-carboxamidine hydrochloride.

In other embodiments, the oligomer having chemically tethered amines is an oligoornithine compound. In another embodiment, the oligoornithine compound is an octaornithine compound (wherein "ornithine" refers to those compounds having longer or side chains than ornithine, as well as ornithine itself), preferably produced by coupling of two tetraornithine compounds, which are in turn preferably produced by coupling of two ornithine dimers.

Still further preferred are those embodiments in which the protected oligomers are polyamides having chemically tethered amines (in protected form), having the formula:

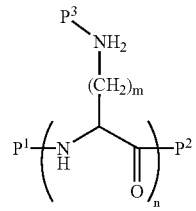

where m, n, $P^1$ and $P^2$ are as defined above, and $P^3$ is an amino-protecting group or in combination with the hydrogen atom on the nitrogen atom to which $P^3$ is attached forms a bivalent amino-protecting group. Preferably m is an integer from 3 to 6, more preferably from 3 to 5. In one particularly preferred group of embodiments, the protected polyamide oligomer compound has the formula above wherein each repeating group is a D-isomer (with stereochemistry corresponding to the D-amino acids).

The aforementioned discussion has focused on oligomers having a peptide backbone, but it is understood that one of skill in the art will readily understand how to apply the methods of the inventions to the synthesis of oligomers having a peptoid, poly-p-phenylene, polyethyleneimine, polyethyleneglycol, peptide-peptoid hybrid, a polyamide, azapeptide, a peptide-urea hybrid, polyenamine, polyenamine, hydrocarbon, polyethylene/polypropylene ether, or carbohydrate backbone. The desired backbone can be purchased commercially or synthesized, then in a single step the chemically tethered amine side chains can be added, followed by the addition of a protecting group removal agent and a guanidinylation reagent to convert each of the protected amines to a guanidinyl group, to produce an oligoguanidine compound.

B. Specific Embodiments of the Methods of the Invention

Accordingly, one embodiment of the invention is a method for the preparation of an oligoguanidine compound, comprising contacting an oligomer having chemically tethered amines, at least a portion of which are protected, with a protecting group removal agent and a guanidinylation reagent to convert each of said protected amines to a guanidinyl group, to produce an oligoguanidine compound. More specifically, the method may comprise the steps of (a) contacting an oligomer having a plurality of chemically tethered amines, wherein a portion of the tethered amines have attached protecting groups, with a protecting group removal agent to remove the protecting groups to produce an oligomer having a plurality of chemically tethered amines; and (b) contacting the resulting oligomer with a guanidiny- Another embodiment of the invention is a method for the preparation of an oligoarginine compound from a suitably protected ornithine monomer, comprising the steps of: (a) coupling two different suitably protected ornithine monomers to produce an orthogonally protected coupled ornithine compound; (b) dividing the orthogonally protected coupled ornithine compound into two portions and activating each of the portions for amide coupling to produce two independently activated coupled ornithine compounds; (c) recombining the two independently activated coupled ornithine compounds under conditions sufficient for amide coupling to produce a new orthogonally protected coupled ornithine compound; (d) subjecting the product of step c) to dividing, activating, and recombining for from zero to three times to produce an oligoornithine compound having 4, 8 or 16 ornithine monomers in a linear configuration; and (e) contacting the oligoornithine compound with a perguanidinylation reagent under conditions sufficient to produce an oligoarginine compound.

In a more general sense, this couple, divide and activate, couple technology can be applied to the assembly of other oligoguanidine compounds wherein each subunit or monomer is selected from an ornithine (or other chemically tethered amine-containing amino acid) and an ornithine that is flanked by one or two amino acids that do not have chemically tethered sidechain amines. The coupling reactions are performed by known coupling methods using known solvents, such as N, N-dimethyl formamide, N-methyl pyrrolidinone, dichloromethane, water, and the like. Exemplary coupling reagents include O-benzotriazolyloxy tetramethyluronium hexafluorophosphate, dicyclohexyl carbodiimide, bromo-tris (pyrrolidino) phosphonium bromide, N, N-dimethylamino pyridine, 4-pyrrolidino pyridine, N-hydroxy succinimide, N-hydroxy benzotriazole, and so forth.

C. Exemplary Method of the Invention

Perguanidininylation has been described for the preparation of guanidinoglycosides (Luedtke et al., *J. Am. Chem. Soc.* 122:12035–12036 (2000) and Feichtinger et al., *J. Org. Chem.* 63:3904–3805 (1998)) and for the perguanidinylation of peptoids (Wender et al., *Proc. Natl. Acad. Sci. USA,* 97:13003–13008 (2000)). Perguanidininylation has now been found to have utility in the preparation of oligoarginine derivatives and spaced arginine transport reagents as described herein.

For example, a suitable synthesis of the arginine octamer 1 was desired due to the utility of this compound as a membrane transport reagent (Rothbard et al., WO 01/13957 and Cooke et al., WO 00/74701). In view of the perguanidinylation studies noted above, octamer 1 could in principle be prepared from an ornithine octamer through a late stage perguanidinylation reaction.

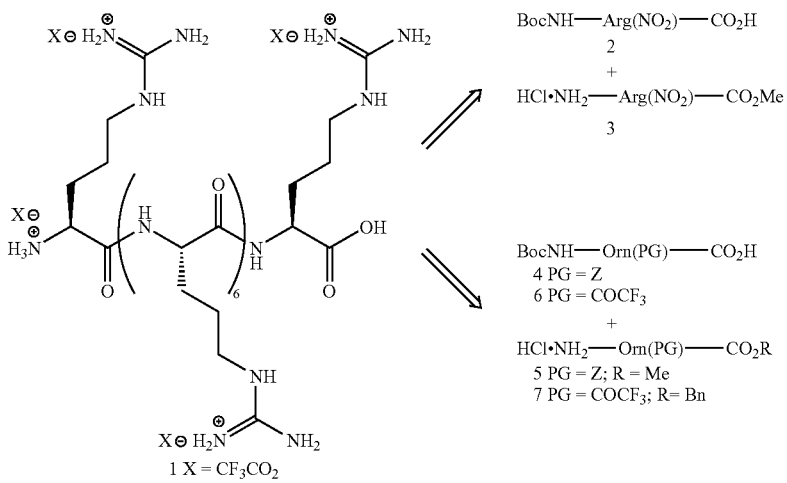

Orthogonally protected ornithine monomers that are commercially available include BocNH-Orn(Z)-CO$_2$H (4) and HCl.NH$_2$-Orn(Z)-CO$_2$Me (5). Thus the orthogonal protecting group strategy for ornithine utilized an acid-labile Boc group on the α-amine, a hydrogenation-labile Z group on the δ-amine, and a base-labile methyl ester on the carboxyl terminus. This strategy yielded promising results at the outset (initial couplings and subsequent deprotections). However, the Z-protected ornithine tetramers, while useful, proved to have limited solubility in organic solvents, necessitating the use of large volumes of solvent for scale up procedures.

In order to improve the solubilities of the ornithine oligomers, an alternative protection strategy was developed. Incorporation of the base-labile trifluoroacetamide protecting group on the δ-amine of ornithine provided more soluble compositions. In addition to α-amine Boc protection, the remaining orthogonal protecting group was a hydrogenation-labile benzyl ester on the carboxyl terminus. The requisite ornithine monomers needed to pursue a bi-directional synthesis of 1, BocNH-Orn(COCF$_3$)—CO$_2$H (6) and HCl.NH$_2$-Orn(COCF$_3$)—CO$_2$Me (7), were prepared from 4, as described in Scheme 1. Protecting group interconversion of the Z group of 4 to the corresponding trifluoroacetamide of 6 was accomplished in quantitative yield by hydrogenation followed by treatment with ethyl trifluoroacetate. Esterification of 6 was accomplished using a known procedure (Kim et al., *J. Org. Chem.,* 50:560–565 (1985)) by treatment with benzyl chloroformate which gave the mixed carbonic anhydride followed by treatment with DMAP (20 mol %) to give 8 in quantitative yield. Finally, removal of the Boc group with HCl gave acid 7 in 98% yield.

Scheme 1

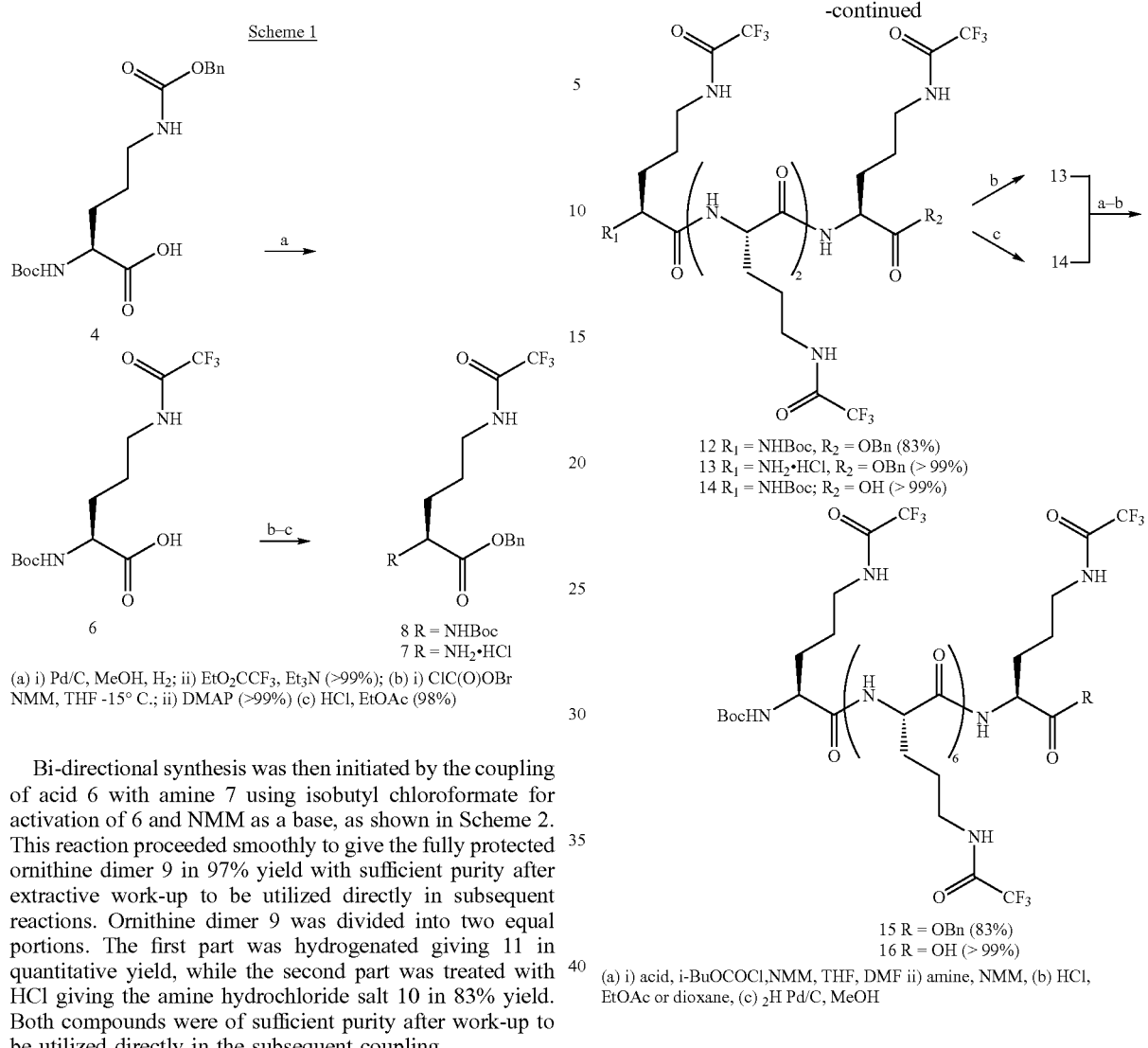

(a) i) Pd/C, MeOH, H$_2$; ii) EtO$_2$CCF$_3$, Et$_3$N (>99%); (b) i) ClC(O)OBr NMM, THF -15° C.; ii) DMAP (>99%) (c) HCl, EtOAc (98%)

Bi-directional synthesis was then initiated by the coupling of acid 6 with amine 7 using isobutyl chloroformate for activation of 6 and NMM as a base, as shown in Scheme 2. This reaction proceeded smoothly to give the fully protected ornithine dimer 9 in 97% yield with sufficient purity after extractive work-up to be utilized directly in subsequent reactions. Ornithine dimer 9 was divided into two equal portions. The first part was hydrogenated giving 11 in quantitative yield, while the second part was treated with HCl giving the amine hydrochloride salt 10 in 83% yield. Both compounds were of sufficient purity after work-up to be utilized directly in the subsequent coupling.

Scheme 2

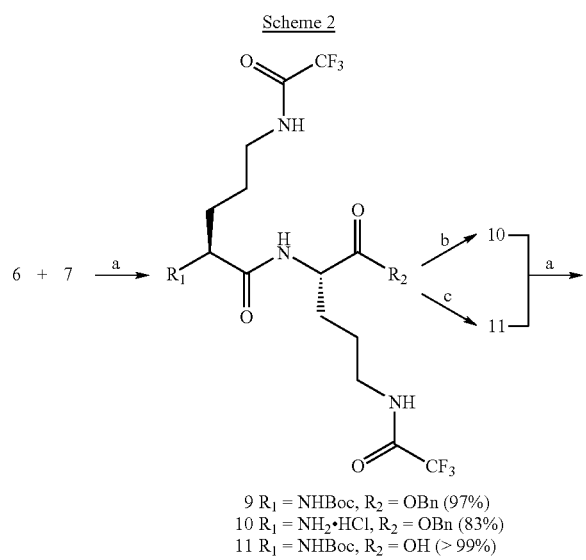

9 R$_1$ = NHBoc, R$_2$ = OBn (97%)
10 R$_1$ = NH$_2$·HCl, R$_2$ = OBn (83%)
11 R$_1$ = NHBoc, R$_2$ = OH (>99%)

(a) i) acid, i-BuOCOCl,NMM, THF, DMF ii) amine, NMM, (b) HCl, EtOAc or dioxane, (c) $_2$H Pd/C, MeOH The ornithine dimers 10 and 11 were subsequently coupled with isobutyl chloroformate and NMM and upon extractive work-up and purification through a short plug of silica gel gave the ornithine tetramer 12 in 83% yield. Compound 12 was readily soluble in ethyl acetate on a multigram (4 g) scale. The fully protected tetramer 12 was then divided into two equal portions and each was subjected to the appropriate conditions for the preparation of the free acid 14 and the amine hydrochloride salt 13, respectively. Coupling 13 and 14 in the usual fashion (isobutyl chloroformate and NMM) proceeded smoothly to give the fully protected ornithine octamer 15 in 83% yield and in sufficient purity to be utilized in subsequent reactions. Hydrogenation of 15 was successful in removing the benzyl ester, giving the free acid 16 in quantitative yield.

Conversion of 16 into the target 1, can be accomplished either in a stepwise fashion (deprotection then perguanidinylation), or via a single operation. Since aqueous sodium carbonate has previously been utilized to effect the deprotection of trifluoroacetamides, (Boger et al., *Org. Chem.* 54:2498–2502 (1989)) and also as one of the reagents in the guanidinylation of amines, (Wender et al., *Proc. Natl. Acad. Sci. USA* 97:13003–13008, (2000) and Bernatowicz et al., *J. Org. Chem.* 57:2497–2502 (1992)) a single step process was investigated. Thus, treatment of the octaornithine derivative 16 with sodium carbonate and pyrazole-1-carboxamidine hydrochloride (17) in aqueous methanol proceeded to give the octaarginine derivative 18 in 51% isolated yield after purification by RP-HPLC (99+% purity) and lyophilization, as shown in Scheme 3.

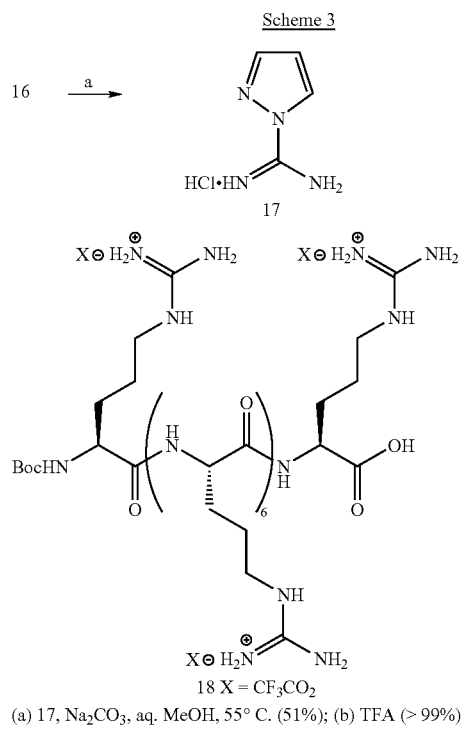

(a) 17, Na$_2$CO$_3$, aq. MeOH, 55° C. (51%); (b) TFA (>99%)

Significantly, eight trifluoroacetamides were converted to eight guanidines in one step (16 transformations overall) under mild conditions. Finally, the synthesis was completed by treatment of 18 with TFA which gave the desired octaarginine product 1 in quantitative yield. Octaarginine 1 was identical in all respects to an authentic sample prepared using Fmoc-based solid-phase synthesis.

IV. Protecting Groups and Protecting Group Removal Agents

As noted above, step (a) of the method of the invention involves contacting an oligomer having a plurality of chemically tethered amines (a portion of the tethered amines having attached protecting groups), with a protecting group removal agent to remove the protecting groups.

The precise conditions and reagents or agents used in this step will depend on the nature of the protecting groups to be removed. Protecting groups selected for the protection of the sidechain- or chemically tethered amine groups are generally those groups that can be removed in the presence of protecting groups in other portions of the oligomer (e.g., the amino or carboxy terminii). Such protecting groups are often referred to as "orthogonal." Generally, the reagents and conditions can be employed by following the guidelines in such protecting group treatises as Greene and Wuts, Protective Groups in Organic Synthesis, 3rd ed., John Wiley & Sons, New York N.Y. (1999), and the references cited therein.

In one embodiment of the invention, the protecting groups on each of the chemically tethered amines are selected from trifluoroacetyl groups, benzyloxycarbonyl groups, and t-butoxycarbonyl groups.

Accordingly, protecting group removal agents will be selected according to the protecting group used. For example, a suitable protecting group removal agent for use with trifluoroacetyl groups is sodium carbonate, preferably in an aqueous alcohol solvent, more preferably in aqueous methanol. Similarly, though less preferred, catalytic hydrogenation can be used (H$_2$ as the protecting group removal agent) to cleave benzyl carbamate (Cbz or simply Z) groups as well as benzyl groups directly attached to the amines. Acids, such as trifluoroacetic acid, can be used to remove t-butoxycarbonyl groups. Still other methods can be used in accordance with the present invention and are well-known to those of skill in the art.

The step of removing the protecting group on the tethered amines can result in the formation of counterions, which include by way of illustration and not limitation, fluorescein, acids having a pKa<13 such as trifluoroacetyl groups (CF$_3$COO—), halo groups (Cl—, F—, Br—, I—), and groups derived from carboxylates (e.g., CH$_3$COO—), carbonates, bicarbonates, phosphates, phosphonates, sulfates, sulfonates, sulfides, borates, silicates, nitrates, nitrites, phenoxides, azides, thiophenoxides, periodates and hypochlorites; and anionic (negatively charged groups) such as SiF$_6$— and BF$_4$—. These counterions can be used alone or can be covalently linked to polycarboxylates, poly-phosphates (as found in nucleic acids and their analogues), polysulfates, polyphosphate/halide combinations and so forth.

V. Guanidinylation Reagents

As noted above, step (b) of the method of the invention involves contacting the oligomer having a plurality of chemically tethered amines, with a guanidinylation reagent to convert each of the chemically tethered amines to a guanidinyl group to produce an oligoguanidine compound.

Any guanidinylation reagent useful for converting an amino group to a guanidino group can be used in the present invention. Preferably, the guanidinylation reagent is a salt of pyrazole-1-carboxamidine. Most preferably, the guanidinylation reagent is pyrazole-1-carboxamidine hydrochloride. Other suitable guanidinylation reagents are described in Bernatowicz et al., *J. Org. Chem.* 57:2497–2502 (1992).

VI. Compounds Produced by the Methods of the Invention

In a general sense, the present invention provides a method for the preparation of compounds having the formula (I):

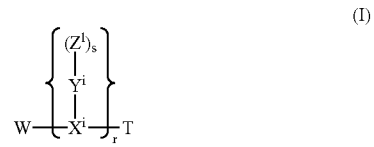

wherein r is an integer of from 4 to 24; T is a protected or unprotected hydroxy group; and W is H or a protecting group. In the subunit portion (enclosed by brackets), s is 0 or 1; each $X^i$ is an amino acid backbone subunit (e.g. —NH—CH—C(O)—), and i is an integer of from 1 to r and denotes the position downstream of W; each $Y^i$ is selected from H, an amino acid sidechain, aryl, and heteroaryl, when s is 0; or is selected from $C_{1-8}$alkylene, $C_{2-8}$alkenylene, $C_{2-8}$alkynylene, $C_{2-8}$heteroalkylene, $C_{3-8}$cycloalkylalkylene, $C_{2-8}$spirocycloalkylene, arylene, heteroarylene, and combinations thereof, when s is 1; each $Z^1$ is a guanidino or guanidinium group.

For example, the bi-directional method of synthesis described herein can be applied to the preparation of oligoarginine compounds (e.g., polymers of 4, 8 or 16 arginine residues) and spaced arginine compounds (e.g., compounds having the formula $(X^0\text{-Arg-}X^0)_q$ or $(X^0\text{-Arg})_q$ wherein q is an integer, typically an even integer of 2, 4, 6, 8, etc, more preferably 2, 4, 6, 8 or 16, and each $X^0$ is an amino acid other than arginine or a guanidine-containing amino acid). In one embodiment, Arg is D-arginine, L-arginine, D-homoarginine or L-homoarginine.

Accordingly, the present invention can be used to prepare, for example, a heptamer or octamer of L-arginine (R7 or R8) (SEQ ID NOS:2–3), D-arginine (r7 or r8), (Gly-Arg-Gly)-(Gly-Arg-Gly)-(Gly-Arg-Gly)-(Gly-Arg-Gly) (SEQ ID NO:4) (wherein Gly-Arg-Gly is the repeating subunit), and shorter or longer oligomers, typically having from 4 to 20 guanidino-containing subunits. In this manner, the methods of the invention can be used to prepare a variety of oligoguanidine compounds including those consisting essentially of from eight to sixteen amino acid residues, where from four to eight of the residues are arginine residues.

Of course, further elaboration of the terminal functional groups (W and T) can lead to compounds having a protected or unprotected linking group, or a linking group having an attached biologically active agent.

In still other embodiments, the oligoguanidine compound that is produced has at least four, preferably at least six, and more preferably at least eight arginine residues, wherein each of the arginine residues is either a D- or L-isomer of the naturally-occurring arginine amino acid. These arginine residues can be contiguous or non-contiguous. For example, the oligoguanidine compound can have at least four or more contiguous arginine residues or the compound can have at least four or more non-contiguous arginine residues.

In another embodiment, the oligoguanidine compound that is produced is converted to a poly trifluoroacetate salt. In general, this conversion is accomplished by contacting the oligoguanidine compound with a suitable amount of trifluoroacetic acid, typically in an aqueous or aqueous/organic mixture.

The couple, divide and activate, couple method described above, find particular utility in producing oligoguanidine compounds wherein each subunit or monomer is selected from an ornithine (or other chemically tethered amine-containing amino acid) and an ornithine that is flanked by one or two amino acids that do not have chemically tethered sidechain amines. Accordingly, in one embodiment of the invention, the oligoarginine compound that is prepared has a formula selected from the group consisting of $(X^0\text{-Arg-}X^0)_t$ and $(X^0\text{-Arg})_t$ wherein each $X^0$ is an amino acid residue that does not have a guanidino moiety; each Arg is selected from the group consisting of D-arginine and L-arginine; and t is an integer selected from 4, 8, 16, 32 and so forth, but is preferably 4, 8, or 16. One of skill in the art will appreciate that the ornithine monomers used to prepare this latter group of oligoarginine compounds are subunits having formula selected from $(X^0\text{-Orn}^p\text{-}X^0)$ and $(X^0\text{-Orn}^p)$ wherein $\text{Orn}^p$ refers to a suitably protected ornithine and each $X^0$ is an amino acid residue that does not have a guanidino moiety or a sidechain amino group (e.g. Lysine). Preferably, each $X^0$ is selected from the group consisting of glycine, β-alanine, 4-aminobutyric acid, 5-aminovaleric acid and 6-aminocaproic acid. In still further preferred embodiments, the oligoarginine compound has a formula of $(X^0\text{-Arg})_t$, each $X^0$ is selected from the group glycine, β-alanine, 4-aminobutyric acid, 5-aminovaleric acid and 6-aminocaproic acid and t is 8 or 16. In a further preferred embodiment, the oligoarginine compound is an octamer of D-arginine or has the formula $(X^0\text{-Arg})_u$, wherein each $X^0$ is glycine, Arg is D-Arg and t is 8.

VII. Conjugates with Compounds Produced by the Methods of the Invention

As noted above, oligoguanidine compounds find utility as transport agents. Accordingly, the invention also relates to the oligoguanidine compounds described herein, that are chemically tethered to a therapeutic agent (which includes active agents and prodrugs thereof).

The oligoguanidine compounds can be tethered to the therapeutic agent in a variety of different ways, as is illustrated below, where T is the oligoguanidine transporter of the invention, D is a suitable therapeutic agent, L is a linker, RL is a releasable linker (e.g., cleavable in vivo) and PD is a prodrug:

Transporter-drug conjugate, T-D T-D, where T-D is active;

Transporter-linker-drug conjugate, T-L-D T-L-D, where T-L-D is active;

Transporter-releasable linker-drug conjugate, T-RL-D RL+D, where T-RL is cleaved and D is active; and Transporter-releasable linker-prodrug conjugate, T-RL-PD T-RL+PD D, where D is active.

As noted in the examples above, the therapeutic agents can be linked to transport agent of the invention in numerous ways, including a direct bond (e.g., with a carbodiimide) or by means of a linking moiety. In particular, carbamate, ester, thioether, disulfide, and hydrazone linkages are generally easy to form and suitable for most applications. In addition, various functional groups (e.g., hydroxyl, amino, halogen, etc.) can be used to attach the therapeutic agent to the transport agent. To help minimize side-reactions, the guanidino moieties can be blocked using conventional protecting groups, such as carbobenzyloxy groups (CBZ), di-t-BOC, PMC, Pbf, N—$NO_2$, and the like. For those therapeutic agents that are inactive until the attached transport agent is released, the linker is preferably a readily cleavable linker, meaning that it is susceptible to enzymatic or solvent-mediated cleavage in vivo. For this purpose, linkers containing carboxylic acid esters and disulfide bonds are preferred, where the former groups are hydrolyzed enzymatically or chemically, and the latter are severed by disulfide exchange, e.g., in the presence of glutathione.

Non-covalent variations of any of the foregoing are also contemplated by the invention, for example:

Transporter-drug complex, T••D T+D, where D is active.

Therapeutic agents that can benefit from the transport agents of the invention include both small organic molecules and macromolecules (e.g., nucleic acids, oligonucleotides, polynucleotides, peptides, polypeptides and proteins). Exemplary therapeutic agents include local and systemic anti-cancer agents, antibiotics, antisense drugs, protease inhibitors, and so forth. In addition, there are numerous releasable linkers that can be used with the transporter compounds of the invention, such as phosphatases, proteases, esterases, redox compounds, photochemical agents, nucleophilic agents, acidic compounds, and so forth. Release of the therapeutic agent can be the result of enzymatic as well as non-enzymatic action.

EXAMPLES

The practice of the present invention will employ, unless otherwise indicated, conventional techniques of synthetic organic chemistry, biochemistry, and the like, which are within the skill of the art. Such techniques are explained fully in the literature. See, for example, *Oligonucleotide Synthesis* (M. J. Gait, ed., 1984); *Nucleic Acid Hybridization* (B. D. Haines & S. J. Higgins, eds., 1984); Kirk-Othmer's *Encyclopedia of Chemical Technology;* and House's *Modern Synthetic Reactions.*

The following examples are put forth so as to provide those of ordinary skill in the art with a complete disclosure and description of how to make and use the compositions/compound/methods of the invention. Efforts have been made to ensure accuracy with respect to numbers (e.g., amounts, temperature, etc.) but some experimental error and deviations should, of course, be allowed for. Unless indicated otherwise, parts are parts by weight, temperature is degrees centigrade and pressure is at or near atmospheric. All components were obtained commercially unless otherwise indicated.

General Methods

BocNH-Orn(Z)-OH (4) was purchased from Novabiochem. All reagents and solvents were purchased from commercial sources and utilized without further purification. Analytical TLC was performed with 0.25 mm silica gel 60F plates with fluorescent indicator (254 nm). Plates were visualized by ultraviolet light and treatment with either ammonium molybdate stain (prepared by combining 90 g of ammonium molybdate, 6 g of cerium sulfate, and 1800 mL of 10% $H_2SO_4$) or potassium permanganate stain (prepared by combining 8 g of $KMnO_4$, 60 g of $K_2CO_3$, 16 mL of 5% NaOH, and 900 mL $H_2O$). RP-HPLC was performed with a Varian ProStar 210/215 HPLC using either a preparative column (Alltec Alltima C18, 250×22 mm) or analytical column (Vydak C18, 150×4.6 mm) with ultraviolet detection of product ($\lambda$=214 nm). The products were eluted utilizing a solvent gradient (solvent A=0.1% $TFA/H_2O$; solvent B=0.1% $TFA/CH_3CN$). Melting points were taken in open capillary tubes utilizing a Thomas Hoover uni-melt apparatus. NMR spectra were measured on a Varian GEM-300 ($^1$H NMR at 300 MHz; $^{13}$C NMR at 75 MHz) magnetic resonance spectrometer. Data for $^1$H NMR spectra are reported as follows: chemical shift, multiplicity (s=singlet, br s=broad singlet, d=doublet, t=triplet, q=quartet, and m=multiplet), integration, and coupling constant (Hz). Data for $^{13}$C NMR spectra are reported in terms of chemical shift relative to residual solvent peak ($D_6$-DMSO=39.5 or $CD_3CN$=1.3). Infrared spectra were recorded on a Perkin-Elmer 1600 Series FTIR. High resolution mass spectra (HRMS) were recorded at the NIH regional mass spectrometry facility at the University of California, San Francisco. Mass spectra utilizing electrospray ionization (ES-MS) were recorded at the mass spectrometry lab at Stanford University utilizing a Finnigan LCQ quadrupole ion trap mass spectrometer.

General Procedure A: Deprotection of Boc-Amides

To a RT stirred solution of Boc-amide (5.0 mmol) in EtOAc (150 mL) or dioxane (300 mL) was bubbled in HCl gas (from a lecture bottle). The reaction mixture was stirred until TLC showed the consumption of the starting material. The desired product was obtained from the reaction mixture (containing precipitate) either by filtration or evaporation of the solvent and used without further purification.

General Procedure B: Deprotection of Benzyl Esters

To a degassed solution of benzyl ester (5.0 mmol) in MeOH (150 mL) was added Pd/C (10% Pd, 250 mg, 0.23 mmol) followed by hydrogen gas (1 atm, balloon). The reaction mixture was stirred at RT until TLC showed complete consumption of the starting material. The reaction mixture was then filtered through Celite and the solvent was removed in vacuo to give the desired product which was used without further purification.

General Procedure C: Amide Coupling

To a room temperature stirred solution of acid (10 mmol) in THF (10 mL) was added DMF (200 mL) and NMM (10.5 mmol). The reaction mixture was cooled to −40° C. and then was treated with a solution of isobutyl chloroformate (10.5 mmol) in THF (10 mL). After stirring at −40° C. for 1 h, the reaction mixture was treated with a solution of amine (10 mmol) and NMM (10 mmol) in DMF (20 mL). The reaction mixture was then allowed to slowly warm up to RT and stirred until TLC revealed the consumption of the starting acid. The reaction mixture was then treated with copious amounts of EtOAc (1 L) and water (1 L). The organic layer was separated and aqueous layer was extracted with EtOAc (2×500 mL). The combined organic layers were washed with an aqueous solution of HCl (0.1 M, 2×500 mL), an aqueous solution of $NaHCO_3$ (5% w/v, 2×500 mL), brine (2×500 mL), and dried over magnesium sulfate. The crude material thus obtained was then purified further as indicated to give the desired product.

Example 1

Synthesis of BocNH-Orn(COCF$_3$)—CO$_2$H (6)

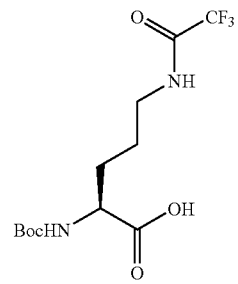

To a degassed solution of acid 4 (25 g, 68 mmol) in MeOH (250 mL) was added Pd/C (10% Pd, 350 mg, 0.33 mmol) followed by hydrogen gas (1 atm, balloon). The reaction mixture was stirred at RT for 12 h by which time TLC showed complete consumption of the starting material. The balloon of hydrogen was then removed and MeOH (100 mL), ethyl trifluoroacetate (14.6 g, 103 mmol), and $Et_3N$ (13.8 g, 136 mmol) were added. The reaction mixture was stirred an additional 9 h and the resulting black suspension was filtered through Celite. A portion of the solvent was then removed in vacuo. The remaining solution (100 mL) was treated with water (150 mL) and EtOAc (100 mL). The organic layer was removed and the aqueous layer was then carefully acidified by the addition of an aqueous solution of HCl (2M). The aqueous layer was extracted with EtOAc (5×80 mL), and the combined organic extracts were then washed with an aqueous solution of HCl (0.1 M, 4×200 mL), brine (200 mL), and dried over magnesium sulfate. Removal of the solvent in vacuo gave the desired product 6 as a viscous oil (22.4 g, 68 mmol, quantitative yield): (Sakarellos et al., *J. Org. Chem.* 43: 293–296 (1978), viscous oil); $R_f$=0.65 (65:31:4 EtOAc/hexane/AcOH); $^1$H NMR (300 MHz, $D_6$-DMSO) δ 12.50 (br s, 1 H), 9.41 (t, 1 H, J=3.2 Hz), 7.11 (d, 1 H, J=4.8 Hz), 3.84–3.87 (m, 1 H), 3.15–3.19 (m, 2 H), 1.51–1.69 (m, 4 H), 1.38 (s, 9 H) ppm; $^{13}$C NMR (75 MHz, $D_6$-DMSO) δ 174.1, 156.2 (q, J=35 Hz), 155.7, 116.0 (q, J=286 Hz), 78.1, 53.2, 38.9, 28.2, 25.2 ppm; IR (thin film) 3316, 1709 cm$^{-1}$; HRMS calculated (M-Boc, $C_7H_{10}F_3N_2O_3$) 227.0644. found 227.0658.

Example 2

Synthesis of BocNH-Orn(COCF$_3$)—CO$_2$Bn (8)

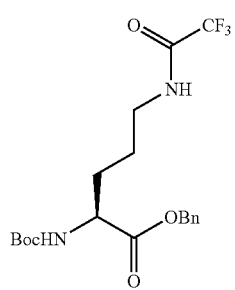

A modification of a known procedure was followed (Kim et al., *J. Org. Chem.* 1985 50, 560–565). To a RT stirred solution of acid 6 (11.3 g, 34.6 mmol) in THF (100 mL) was added NMM (3.50 g, 34.6 mmol) and the reaction mixture was cooled to −15° C. (NaCl/ice/water bath). To the cooled reaction mixture was added a solution of benzyl chloroformate (6.17 g, 36.1 mmol) in THF (5 mL). After stirring at −15° C. for 2 min, the reaction mixture was warmed to 0° C. (ice/water bath) and stirred for 15 min. To the reaction mixture was added DMAP (1.05 g, 8.65 mmol) and reaction mixture was allowed to warm to RT and stirred for 2 h. The reaction mixture was then treated with EtOAc (100 mL), water (100 mL), and carefully acidified with an aqueous solution of HCl (1 M). The organic layer was separated and washed with an aqueous solution of HCl (0.1 M, 2×50 mL). The combined aqueous layers were then extracted with EtOAc (2×100 mL). The combined organic layers were washed with an aqueous solution of NaHCO$_3$ (5% w/v, 4×50 mL), brine (100 mL), and dried over magnesium sulfate. Removal of the solvent in vacuo gave the desired product 8 as a white amorphous solid (14.2 g, 33.9 mmol, 98% yield): mp 72–73.5° C.; $R_f$=0.58 (3:7 EtOAc/hexane); $^1$H NMR (300 MHz, $D_6$-DMSO) δ 9.39 (t, 1 H, J=5.1 Hz), 7.32–7.37 (m, 5 H), 5.04–5.16 (m, 2 H, rotamers), 3.94–4.06 (m, 1 H), 3.12–3.18 (m, 2 H), 1.45–1.70 (m, 4 H), 1.36 (s, 9 H) ppm; $^{13}$C NMR (75 MHz, $D_6$-DMSO) δ 172.4, 156.2 (q, J=35 Hz), 155.6, 136.0, 128.4, 128.0, 127.7, 116.0 (q, J=286 Hz), 78.3, 65.8, 53.4, 28.2, 27.8, 25.0 ppm (CH$_2$—NHCOCF$_3$ peaks obscured by residual $D_6$-DMSO); IR (thin film) 3333, 1709 cm$^{-1}$; HRMS calculated (M+2H−Boc, $C_{14}H_{18}F_3N_2O_3$) 319.1270. found 319.1215.

Example 3

Synthesis of HCl.NH$_2$-Orn(COCF$_3$)—CO$_2$Bn (7)

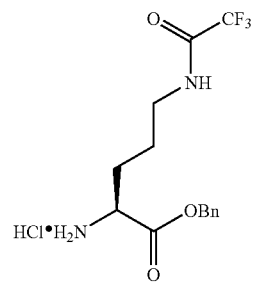

General procedure A with protected ornithine 6 (14.2 g, 33.9 mmol), EtOAc (150 mL), and reaction time=12 h. Evaporation of the solvent gave the desired product 7 as a white powder (12.0 g, 33.8 mmol, quantitative yield): mp 187–188° C.; $R_f$=0.33 (25:1 EtOAc/Et$_3$N); $^1$H NMR (300 MHz, $D_6$-DMSO) δ 9.61 (t, 1 H, J=3.3 Hz), 8.71 (br s, 3 H), 7.36–7.43 (m, 5 H), 5.24 (s, 2 H), 4.11 (t, 1 H, J=3.8 Hz), 3.17–3.21 (m, 2 H), 1.81–1.86 (m, 2H), 1.62–1.68 (m, 1 H), 1.52–1.56 (m, 1 H) ppm; $^{13}$C NMR (75 MHz, $D_6$-DMSO) δ 169.3, 156.3 (q, J=35 Hz), 135.2, 128.5, 128.4, 116.0 (q, J=286 Hz), 67.1, 51.6, 38.5, 27.4, 24.0 ppm; IR (thin film) 3314, 3211, 1740, 1699 cm$^{-1}$; HRMS calculated (M+H, $C_{14}H_{18}F_3N_2O_3$) 319.1270. found 319.1257.

Example 4

Synthesis of BocNH-(Orn(COCF$_3$))$_2$—CO$_2$Bn (9)

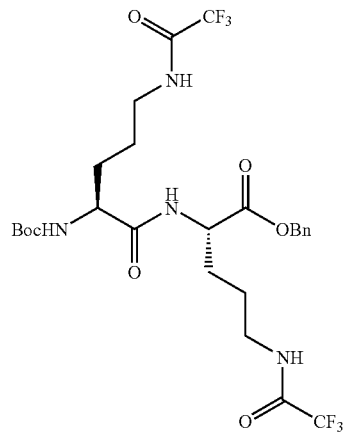

General procedure C with acid 6 (4.69 g, 14.3 mmol) and amine 7 (5.01 g, 14.3 mmol). After work-up, removal of the solvent in vacuo gave the desired product 9 as a white powder (8.75 g, 13.9 mmol, 97% yield): mp 160–162° C.; $R_f$=0.80 (1:1 EtOAc/hexane); $^1$H NMR (300 MHz, $D_6$-DMSO) δ 9.44 (t, 1 H, J=3.2 Hz), 9.40 (t, 1 H, J=3.2 Hz), 8.27 (d, 1 H, J=4.2 Hz), 7.32–7.39 (m, 5 H), 6.90 (d, 1 H, J=4.8 Hz), 5.11 (s, 2 H), 4.31–4.35 (m, 1 H), 3.94 (br m, 1 H), 3.10–3.19 (m, 4 H), 1.72–1.76 (m, 1 H), 1.37–1.66 (m, 7 H), 1.37 (s, 9 H) ppm; $^{13}$C NMR (75 MHz, $D_6$-DMSO) δ 172.4, 171.7, 156.3 (q, J=35 Hz), 155.3, 135.9, 128.4, 128.1, 116.0 (q, J=286 Hz), 78.1, 66.0, 53.7, 51.6, 29.2, 28.2, 28.1, 25.0, 24.8 ppm (CH$_2$—NHCOCF$_3$ peaks obscured by residual D$_6$-DMSO); IR (thin film) 3313, 1704 cm$^{-1}$; HRMS calculated (M+2 H–Boc, C$_{21}$H$_{27}$F$_6$N$_4$O$_5$) 529.1886. found 529.1889.

Example 5

Synthesis of HCl.NH$_2$-(Orn(COCF$_3$))$_2$—CO$_2$Bn (10)

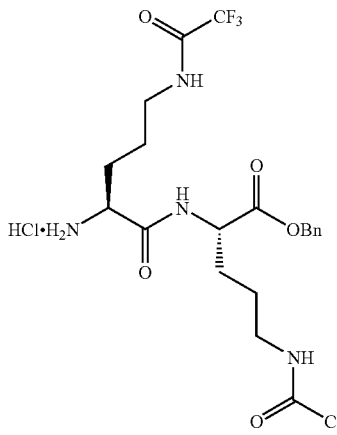

See general procedure A with protected di-ornithine 9 (3.8 g, 6.0 mmol), EtOAc (150 mL), reaction time=12 h. After filtration of the reaction mixture, washing the solid (EtOAc), and drying in vacuo, the desired product 10 was obtained as a white powder (2.9 g, 5.0 mmol, 83% yield): mp 191–194° C.; $^1$H NMR (300 MHz, D$_6$-DMSO) δ 9.52–9.64 (m, 2 H), 9.04–9.11 (m, 1 H), 8.35 (br s, 3 H), 7.30–7.38 (m, 5 H), 5.12 (s, 2 H), 4.32–4.40 (m, 1 H), 3.80–3.88 (m, 1 H), 3.06–3.25 (m, 4 H), 1.49–1.84 (m, 8 H) ppm; $^{13}$C NMR (75 MHz, D$_6$-DMSO) δ 171.2, 168.9, 156.3 (q, J=35 Hz), 135.8, 128.5, 128.2, 128.0, 116.0 (q, J=286 Hz), 66.2, 51.8, 51.6, 38.6, 28.5, 27.8, 24.7, 23.8 ppm (CH$_2$—NHCOCF$_3$ peaks obscured by residual D$_6$-DMSO); IR (thin film) 3305, 1701, 1659 cm$^{-1}$; HRMS calculated (M+H, C$_{21}$H$_{27}$F$_6$N$_4$O$_5$) 529.1886. found 529.1881.

Example 6

Synthesis of BocNH-(Orn(COCF$_3$))$_2$—CO$_2$H (11)

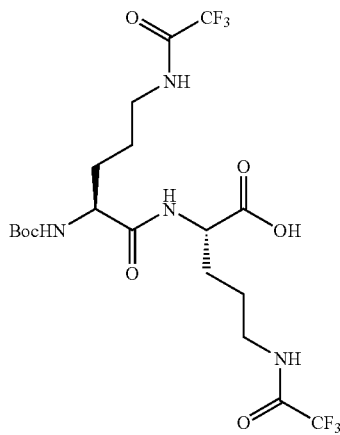

See general procedure B with protected di-ornithine 9 (3.8 g, 6.0 mmol) and reaction time=12 h. After work-up, the desired product 11 was obtained as a white foam (3.3 g, 6.0 mmol, quantitative): mp 149–151° C.; R$_f$=0.44 (65:31:4 EtOAc/hexane/AcOH); $^1$H NMR (300 MHz, D$_6$-DMSO) δ 9.35–9.48 (m, 2 H), 8.00–8.06 (m, 1 H), 6.85–6.93 (m, 1 H), 4.14–4.23 (m, 1 H), 3.86–3.94 (br m, 1 H), 3.12.3.22 (m, 4 H), 1.44–1.76 (m, 8 H), 1.35 (s, 9 H) ppm; $^{13}$C NMR (75 MHz, D$_6$-DMSO) δ 173.4, 172.1, 157.0 (q, J=35 Hz), 155.3, 116.0 (q, J=286 Hz), 78.1, 53.8, 51.4, 39.0, 38.8, 29.2, 28.4, 28.2, 25.0, 24.8 ppm; IR (thin film) 3309, 1713 cm$^{-1}$; HRMS calculated (M–t-BuO, C$_{15}$H$_{19}$F$_6$N$_4$O$_6$) 465.1209. found 465.1205.

Example 7

Synthesis of BocNH-(Orn(COCF$_3$))$_4$—CO$_2$Bn (12)

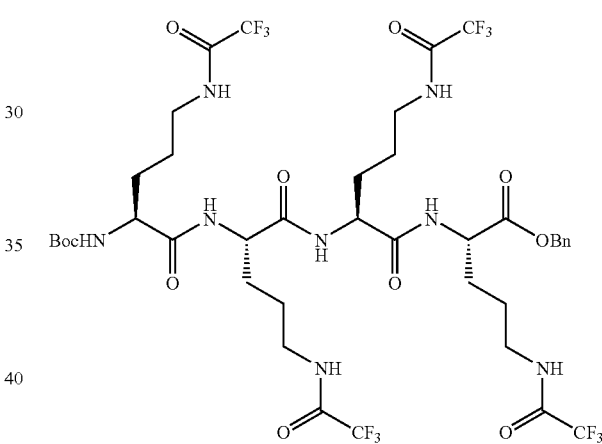

See general procedure C with acid 11 (2.60 g, 4.82 mmol) and amine 10 (2.72 g, 4.82 mmol). After work-up, the crude solid was taken up in solution (9:1 EtOAc/MeOH) and passed through a short plug of silica gel. Removal of the solvent in vacuo gave the desired product 12 as a white powder (4.20 g, 4.00 mmol, 83% yield): mp 197–198° C.; R$_f$=x (solvent); $^1$H NMR (300 MHz, D$_6$-DMSO) δ 8.72–8.77 (m, 4 H), 7.72 (d, 1 H, J=7.5 Hz), 7.39 (d, 1 H, J=7.8 Hz), 7.17 (d, 1 H, J=7.8 Hz), 6.66–6.73 (m, 5 H), 6.33 (d, 1 H, J=8.1 Hz), 4.45 (s, 3 H), 3.95 (m, 1H), 3.15 (m, 8H), 1.30–1.74 (m, 25H) ppm; $^{13}$C NMR (75 MHz, D$_6$-DMSO) δ 172.3, 171.9, 171.6, 171.2, 156.2 (q, J=35 Hz), 155.4, 135.9, 128.4, 128.1, 127.9, 116.0 (q, J=286 Hz), 78.2, 66.0, 54.0, 51.8, 51.7, 51.6, 29.8, 29.6, 29.0, 28.1, 27.9, 25.0, 24.8, 24.7, 18.9 ppm (CH$_2$—NHCOCF$_3$ peaks obscured by residual D$_6$-DMSO); IR (thin film) 3306, 1707 cm$^{-1}$; HRMS calculated (M+H, C$_{40}$H$_{53}$F$_{12}$N$_8$O$_{11}$) 1049.4. found 1049.0.

Example 8

Synthesis of HCl.NH$_2$-(Orn(COCF$_3$))$_4$—CO$_2$Bn (13)

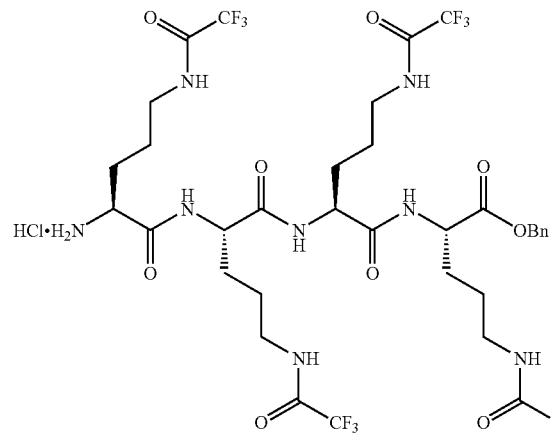

See general procedure A with protected tetra-ornithine 12 (2.0 g, 1.9 mmol), dioxane (300 mL), and reaction time=18 h. After concentration of the solvent in vacuo, the desired product 13 was obtained as a yellow amorphous solid (1.9 g, 1.9 mmol, quantitative yield): mp 238–240° C.; $^1$H NMR (300 MHz, D$_6$-DMSO) δ 9.44–9.51 (m, 4 H), 8.62 (d, 1 H, J=7.8 Hz), 8.44 (d, 1 H, J=7.2 Hz), 8.15–8.20 (m, 4 H), 7.30–7.35 (m, 5 H), 5.09 (s, 2 H), 4.26–4.35 (m, 3 H), 3.75–3.81 (m, 1 H), 3.10–3.20 (m, 8 H), 1.40–1.72 (m, 16 H) ppm; $^{13}$C NMR (75 MHz, D$_6$-DMSO) δ 171.7, 171.6, 170.8, 168.3, 156.2 (q, J=36 Hz), 135.8, 128.4, 128.1, 127.8, 116.0 (q, J=286 Hz), 66.4, 66.0, 52.2, 51.9, 51.7, 29.6, 29.5, 28.64, 28.56, 27.9, 24.8, 24.7, 24.0 ppm (CH$_2$—NHCOCF$_3$ peaks obscured by residual D$_6$-DMSO); IR (nujol mull) 3302, 2914, 1702, 1671, 1641, 1562, 1528, 1461, 1377, 1182, 724 cm$^{-1}$; ES-MS (+ ionization) calculated (M+H, C$_{35}$H$_{45}$F$_{12}$N$_8$O$_9$) 949.3. found 949.4.

Example 9

Synthesis of BocNH-(Orn(COCF$_3$))$_4$—CO$_2$H (14)

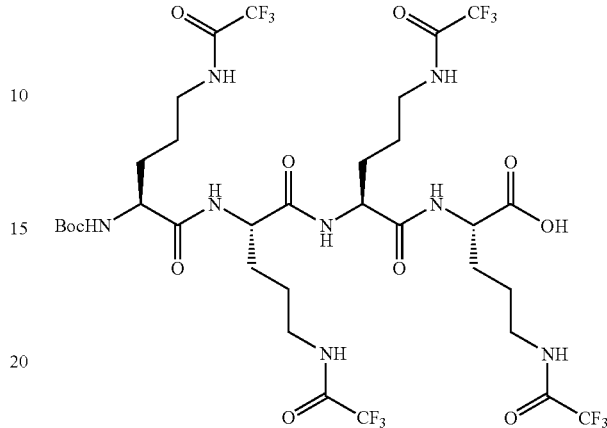

See general procedure B with protected tetra-ornithine 12 (2.0 g, 1.9 mmol) and reaction time=16 h. After work-up, the desired product 14 was obtained as a white foam (1.8 g, 1.9 mmol, quantitative yield): mp 90–105° C.; R$_f$=0.34 (65:31:4 EtOAc/hexane/AcOH); $^1$H NMR (300 MHz, D$_6$-DMSO) δ 9.34–9.43 (m, 4 H), 8.17 (d, 1 H, J=7.5 Hz), 8.02 (d, 1 H, J=8.1 Hz), 7.82 (d, 1 H, J=8.1 Hz), 6.98 (d, 1 H, J=7.8 Hz), 4.23–4.30 (br m, 2 H), 4.12–4.18 (m, 1 H), 3.85–3.90 (m, 1 H), 3.10–3.18 (br m, 8 H), 1.47–1.68 (m, 16 H), 1.35 (s, 9 H) ppm; $^{13}$C NMR (75 MHz, D$_6$-DMSO) δ 173.2, 171.9, 171.4, 171.2, 156.2 (q, J=35 Hz), 155.4, 116.0 (q, J=286 Hz), 78.2, 54.0, 51.9 (2 C), 51.5, 39.4, 38.8, 29.8, 29.6, 29.0, 28.3, 28.1, 25.0, 24.9, 24.8, 24.7 ppm (CH$_2$—NHCOCF$_3$ peaks obscured by residual D$_6$-DMSO); IR (thin film) 3306, 1709, 1664 cm$^{-1}$; ES-MS (+ ionization) calculated (M+H, C$_{33}$H$_{47}$F$_{12}$N$_8$O$_{11}$) 959.3. found 959.3.

Example 10

Synthesis of BocNH-(Orn(COCF$_3$))$_8$—CO$_2$Bn (15)

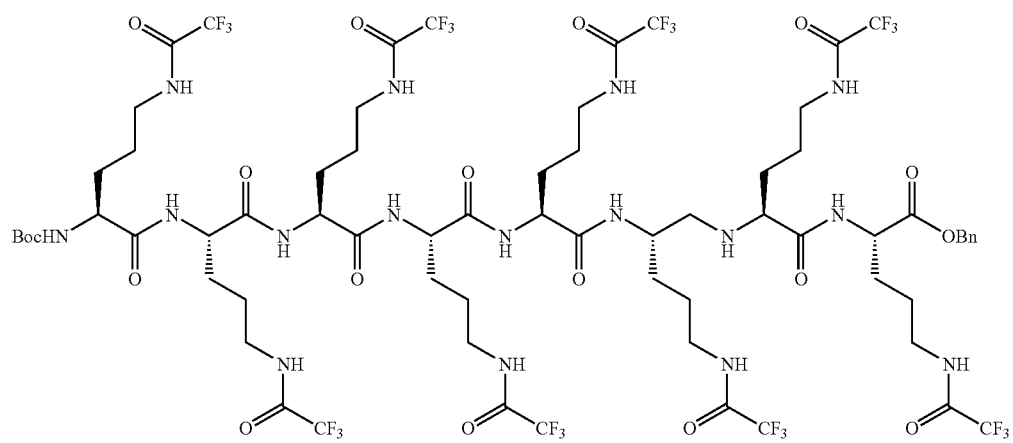

See general procedure C with acid 14 (300 mg, 0.313 mmol) and amine 13 (308 mg, 0.313 mmol). After work-up, the desired product 15 was obtained as a white amorphous solid (490 mg, 0.259 mmol, 83% yield): mp 225–226° C. (dec); $R_f$=0.75 (95:5 EtOAc/MeOH); $^1$H NMR (300 MHz, $D_6$-DMSO) δ 9.30–9.45 (m, 7 H), 8.37 (d, 1 H, J=6.6 Hz), 7.90–8.08 (m, 4 H), 7.84 (d, 1 H, J=7.5 Hz), 7.25–7.36 (m, 5 H), 6.97 (m, 1 H, J=7.5 Hz), 5.09 (s, 2 H), 4.20–4.35 (m, 7 H), 3.82–3.91 (m, 1 H), 2.99–3.18 (m, 16 H), 1.25–1.80 (m, 32 H), 1.35 (s, 9 H) ppm; $^{13}$C NMR (75 MHz, $D_6$-DMSO) δ 172.0, 171.7, 171.6, 171.4, 171.3, 171.2, 156.3 (q, J=35 Hz), 155.4, 135.9, 128.4, 128.1, 127.9, 116.0 (q, J=286 Hz), 78.2, 66.0, 54.1, 52.1, 51.8, 51.7, 29.7, 29.4, 29.0, 28.1, 28.0, 25.0, 24.8, 18.9 ppm ($\underline{C}H_2$—NHCOCF$_3$ peaks obscured by residual $D_6$-DMSO); IR (thin film) 3293, 3100, 2944, 1705, 1659, 1548, 1444, 1370, 1156 cm$^{-1}$; ES-MS (+ ionization) calculated (M+H, $C_{68}H_{89}F_{24}N_{16}O_{19}$) 1889.6. found 1889.2.

Example 11

Synthesis of BocNH-(Orn(COCF$_3$))$_8$—CO$_2$H (16)

See general procedure B with protected octa-ornithine 15 (36 mg, 0.019 mmol), Pd/C (10%, 10 mg, 0.0094 mmol), MeOH (3 mL), and reaction time=3 h. After work-up, the desired product 16 was obtained as a white powder (34 mg, 0.019 mmol, quantitative yield): mp 235–239° C. (dec); $R_f$=0.80 (4:1 EtOAc/MeOH); $^1$H NMR (300 MHz, 2:1 CD$_3$CN/D$_2$O) δ 8.70–8.79 (m, 3 H), 7.55–7.68 (m, 4 H), 4.08–4.26 (m, 7 H), 3.21 (br m, 16 H), 1.49–1.74 (m, 32 H), 1.35 (s, 9 H) ppm; $^{13}$C NMR (75 MHz, 2:1 CD$_3$CN/D$_2$O) δ 175.6, 174.8, 174.7, 174.6, 174.1, 173.6, 173.5, 173.4, 158.5 (q, J=36 Hz), 157.7, 117.0 (q, J=280 Hz), 81.2, 56.1, 55.5, 55.2, 54.9, 54.4, 53.9, 53.4, 53.0, 39.9 (m), 25.5–29.4 (m) ppm; IR (thin film) 3305, 1704, 1658 cm$^{-1}$; ES-MS (– ionization) calculated ($C_{61}H_{83}F_{24}N_{16}O_{19}$—H) 1798.6. found 1799.2.

Example 12

Synthesis of BocNH-Arg$_8$-CO$_2$H (.8TFA salt) (18)

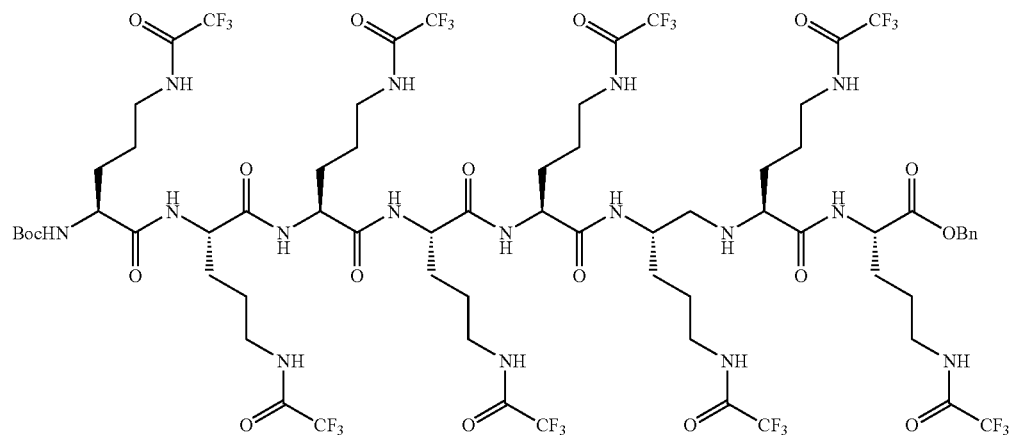

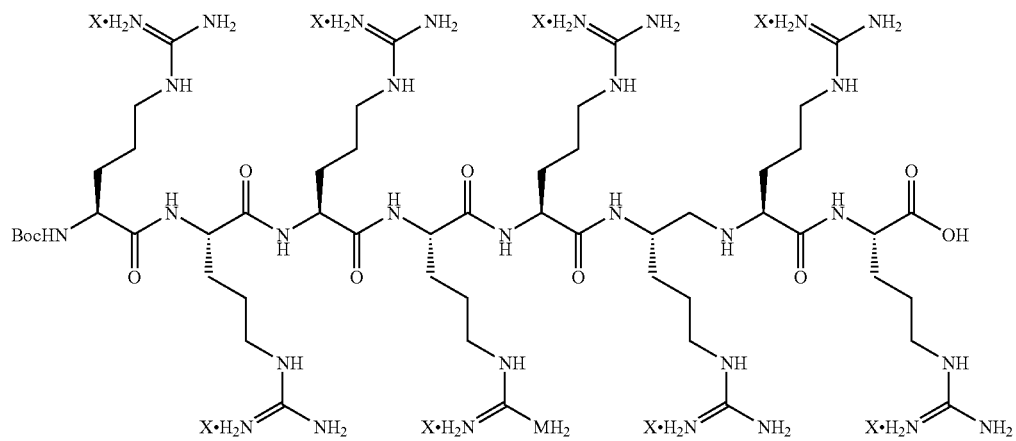

X = TFA

To a solution of 16 (143 mg, 0.080 mmol) in MeOH (3 mL) was added sodium carbonate (345 mg, 3.26 mmol), pyrazole-1-carboxamidine hydrochloride (17) (478 mg, 3.26 mmol), and deionized water (6 mL). The solution was heated at 55° C. for 36 h and then the reaction mixture was carefully acidified by the addition of TFA (to pH~4). The solvent was removed in vacuo giving a white residue which was purified using RP-HPLC (isocratic: 5% solvent A, 5 min; gradient: 5% solvent A to 50% solvent A, 19 min). Lyophilization of the major product ($R_t$=15.2 min) gave the desired product as a white powder 18 (93 mg, 0.041 mmol, 51% yield): analytical RP-HPLC (gradient: 5% solvent A to 95% solvent A, 15 min) $R_t$=4.64 min, 99+% purity; $^1$H NMR (300 MHz, $D_6$-DMSO) δ 8.20–8.28 (m, 3 H), 4.05–4.22 (m, 7 H), 3.80–3.90 (m, 1 H), 2.99–3.10 (m, 16 H), 1.40–1.82 (m, 32 H), 1.26 (s, 9 H) ppm; $^{13}$C NMR (75 MHz, $D_6$-DMSO) δ 169.7, 168.0, 167.92, 167.89, 167.8, 157.5 (q, J=36 Hz, TFA C=O), 152.1, 151.3, 111.0 (q, J=290 Hz, TFA $CF_3$), 76.2, 49.2, 48.0, 47.9, 47.1, 35.1, 22.9, 22.3, 22.2, 19.1 ppm; ES-MS (− ionization) calculated ($C_{53}H_{106}N_{32}O_{11}$—H) 1365.9. found 1365.8.

Example 13

Synthesis of 9TFA.$NH_3$-$Arg_8$-$CO_2H$ (1)

A solution of 18 (85 mg, 0.037 mmol) in trifluoroacetic acid (3 mL) with 150 μL of triisopropyl silane was stirred at RT for 30 min. To the reaction mixture was added deionized water (3 mL) and the solvent was then removed by lyophilization. The resulting crude residue was purified by RP-HPLC (isocratic: 5% solvent A, 5 min; gradient: 5% solvent A to 50% solvent A, 19 min). Lyophilization of the major product ($R_t$=12.8 min) gave the desired product 1 (85 mg, 0.037 mmol, >99% yield) as a white powder: analytical RP-HPLC (gradient: 5% solvent A to 95% solvent A, 15 min) $R_t$=4.6 min, 99+% purity; mp 105–108 ° C.; $^1$H NMR (300 MHz, $D_2O$) δ 8.33–8.50 (m, 3 H), 4.12–4.25 (m, 7 H), 3.90 (t, 1 H, J=6.6 Hz), 3.02–3.10 (m, 14 H), 2.87 (t, 2 H, J=6.3 Hz), 1.40–1.82 (m, 32 H) ppm; $^{13}$C NMR (75 MHz, $D_2O$) δ 169.9, 168.0, 167.9, 167.7, 164.1, 157.6 (q, J=35 Hz, TFA C=O), 151.4, 111.0 (q, J=290 Hz, TFA $CF_3$), 48.1, 48.0, 47.8, 47.3, 47.1, 35.2, 35.1, 35.0, 33.5, 23.0, 22.9, 22.7, 22.3, 19.1, 18.9, 18.1, 17.9 ppm; ES-MS (− ionization) calculated ($C_{48}H_{98}N_{32}O_9$—H) 1265.8. found 1265.9.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

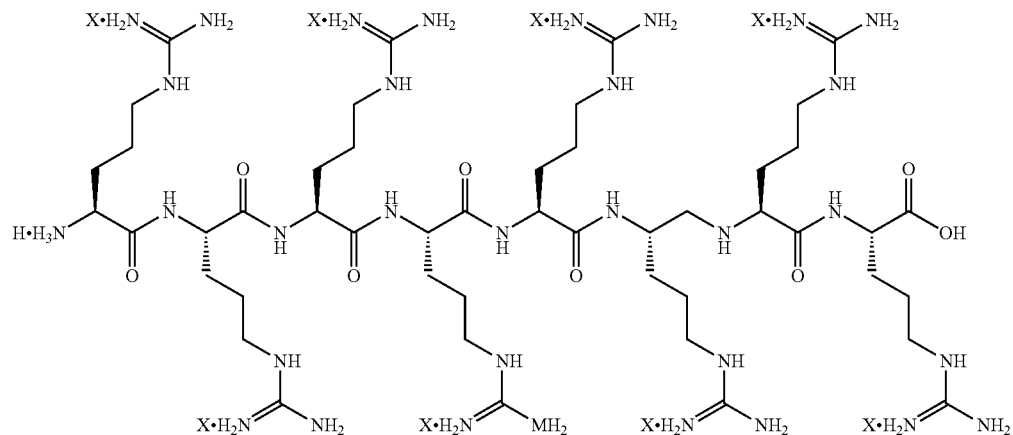

X = TFA

We claim:

1. A method for the preparation of an oligoguanidine compound, comprising:
   (a) contacting an oligomer having a plurality of chemically tethered amines, wherein a portion of said tethered amines have attached protecting groups, with a protecting group removal agent to remove said protecting groups to produce an oligomer having a plurality of chemically tethered amines; and
   (b) contacting said oligomer having a plurality of chemically tethered amines with a salt of pyrazole-1-carboxamidine to convert each of said chemically tethered amines to a guanidinyl group to produce an oligoguanidine compound;
   wherein the contacting of steps (a) and (b) is carried out in solution.

2. The method of claim 1, wherein the protecting groups on each of the chemically tethered amines are trifluoroacetyl groups.

3. The method of claim 1, wherein both of the contacting steps are conducted in a single reaction vessel.

4. The method of claim 1, wherein the contacting steps are carried out sequentially.

5. The method of claim 1, wherein the contacting steps are carried out concurrently.

6. The method of claim 1, wherein the oligomer has a peptide backbone.

7. The method of claim 6 wherein the peptide backbone is a cyclic peptide backbone.

8. The method of claim 6, wherein the oligomer is an oligoornithine compound.

9. The method of claim 8, wherein the oligoornithine compound is an octaornithine compound and is produced by coupling of two tetraornithine compounds.

10. The method of claim 9, wherein each of the tetraornithine compounds are produced by the coupling of two ornithine dimers.

11. The method of claim 1, wherein the oligomer has a non-peptide backbone selected from the group consisting of peptoid, poly-p-phenylene, polyethyleneglycol, peptide-peptoid hybrid, a polyamide, azapeptide, a peptide-urea hybrid, polyenamine, polyoxamide, hydrocarbon, polyethylene/polypropylene ether, carbohydrate, and oxy-substituted dicyclohexyl ether.

12. The method of claim 11, wherein the non-peptide backbone is a cyclic non-peptide backbone.

13. The method of claim 1, wherein the oligoguanidine compound has at least four arginine residues.

14. The method of claim 13, wherein the oligoguanidine compound has at least six arginine residues.

15. The method of claim 14, wherein the oligoguanidine compound comprises at least eight arginine residues that are contiguous.

16. The method of claim 15, wherein the oligoarginine compound is an octamer of D-arginine or L-arginine.

17. The method of claim 13, wherein the oligoguanidine compound comprises from four to eight arginine residues that are non-contiguous.

18. The method of claim 1, wherein the oligoguanidine compound consists essentially of from eight to sixteen amino acid residues, wherein from four to eight of the amino acid residues are arginine residues.

19. The method of claim 13, wherein the arginine residues are selected from the group consisting of D-arginine, L-arginine, D-homoarginine and L-homoarginine.

20. The method of claim 19, wherein the arginine residues are selected from the group consisting of D-arginine and L-arginine.

21. The method of claim 1, wherein the oligoguanidine compound has a formula selected from the group consisting of $(X^0\text{-Arg-}X^0)_q$ and $(X^0\text{-Arg})_q$ wherein each $X^0$ is an amino acid residue that does not have a guanidino moiety; Arg is selected from the group consisting of D-arginine, L-arginine, D-homoarginine and L-homoarginine; and q is an integer selected from 2, 4, 6, 8 and 16.

22. The method of claim 22, wherein the oligoguanidine compound has the formula $(X^0\text{-Arg-}X^0)_q$.

23. The method of claim 21, wherein the oligoguanidine compound has the formula $(X^0\text{-Arg})_q$.

24. The method of claim 13, wherein the side chains of the arginine residues are modified.

25. The method of claim 22, wherein the side chains of the arginine residues are modified to include a C, O, N, S or B derivative.

26. The method of claim 24, wherein the side chains of the arginine residues are modified to include a double or a triple bond.

27. The method of claim 24, wherein the side chains of the arginine residues are modified to include a cyclic structure.

28. The method of claim 1, wherein the guanidinyl groups are modified.

29. The method of claim 1, which further comprises the step of converting the oligoguanidine compound to a salt.

30. The method of claim 29, wherein the salt is a poly trifluoroacetate salt.

* * * * *

SEQUENCE LISTING

<160> NUMBER OF SEQ ID NOS: 4

<210> SEQ ID NO 1
<211> LENGTH: 24
<212> TYPE: PRT
<213> ORGANISM: Artificial sequence
<220> FEATURE:
<223> OTHER INFORMATION: Chemically synthesized peptide.
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (8)..(8)
<223> OTHER INFORMATION: Orn
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (14)..(14)
<223> OTHER INFORMATION: Orn
<220> FEATURE:
<221> NAME/KEY: MOD_RES
<222> LOCATION: (17)..(17)
<223> OTHER INFORMATION: Orn
<220> FEATURE:
<221> NAME/KEY: MOD_RES
<222> LOCATION: (20)..(20)
<223> OTHER INFORMATION: Orn
<220> FEATURE:
<221> NAME/KEY: MOD_RES
<222> LOCATION: (23)..(23)
<223> OTHER INFORMATION: Orn

<400> SEQUENCE: 1

Gly Xaa Gly Gly Xaa Gly Gly Xaa Gly Gly Xaa Gly Gly Xaa Gly Gly
1               5                   10                  15

Xaa Gly Gly Xaa Gly Gly Xaa Gly
            20

<210> SEQ ID NO 2
<211> LENGTH: 7
<212> TYPE: PRT
<213> ORGANISM: Artificial sequence
<220> FEATURE:
<223> OTHER INFORMATION: Chemically synthesized peptide.

<400> SEQUENCE: 2

Arg Arg Arg Arg Arg Arg Arg
1               5

<210> SEQ ID NO 3
<211> LENGTH: 8
<212> TYPE: PRT
<213> ORGANISM: Artificial sequence
<220> FEATURE:
<223> OTHER INFORMATION: Chemically synthesized sequence

<400> SEQUENCE: 3

Arg Arg Arg Arg Arg Arg Arg Arg
1               5

```
<210> SEQ ID NO 4
<211> LENGTH: 15
<212> TYPE: PRT
<213> ORGANISM: Artificial sequence
<220> FEATURE:
<223> OTHER INFORMATION: Chemically synthesized peptide

<400> SEQUENCE: 4

Gly Arg Gly Gly Arg Gly Gly Arg Gly Gly Arg Gly Gly Arg Gly
1               5                   10                  15
```